US012616455B2

(12) United States Patent
Velev et al.

(10) Patent No.: US 12,616,455 B2
(45) Date of Patent: May 5, 2026

(54) HYDROGEL-ENABLED MICROFLUIDIC SWEAT SEQUESTERING FOR WEARABLE HUMAN-DEVICE INTERFACES

(71) Applicant: North Carolina State University, Raleigh, NC (US)

(72) Inventors: Orlin D. Velev, Raleigh, NC (US); Timothy W. Shay, Milwaukee, WI (US); Michael D. Dickey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 1385 days.

(21) Appl. No.: 16/618,734

(22) PCT Filed: Jun. 2, 2018

(86) PCT No.: PCT/US2018/035761
§ 371 (c)(1),
(2) Date: Dec. 2, 2019

(87) PCT Pub. No.: WO2018/223105
PCT Pub. Date: Dec. 6, 2018

(65) Prior Publication Data
US 2020/0163656 A1 May 28, 2020

Related U.S. Application Data

(60) Provisional application No. 62/514,232, filed on Jun. 2, 2017.

(51) Int. Cl.
*A61B 10/00* (2006.01)
*A61B 5/145* (2006.01)
(Continued)

(52) U.S. Cl.
CPC ...... *A61B 10/0064* (2013.01); *A61B 5/14514* (2013.01); *A61B 5/14517* (2013.01);
(Continued)

(58) Field of Classification Search
CPC ........... A61B 10/0064; A61B 5/14514; A61B 5/14517; A61B 5/14532; A61B 5/150061;
(Continued)

(56) References Cited

U.S. PATENT DOCUMENTS

2009/0087884 A1     4/2009  Beerling et al.
2009/0087925 A1*    4/2009  Wagner ............... B01F 25/4317
                                                                    436/63
(Continued)

FOREIGN PATENT DOCUMENTS

WO       2015138978 A1     9/2015
WO       2016025468 A2     2/2016

OTHER PUBLICATIONS

International Search Report mailed Jan. 21, 2019.
(Continued)

*Primary Examiner* — Jennifer Robertson
*Assistant Examiner* — Jonathan Drew Moroneso
(74) *Attorney, Agent, or Firm* — THOMAS | HORSTEMEYER, LLP

(57) ABSTRACT

Microfluidic devices are provided for continuous sampling of biological fluid for extended periods of time, e.g. for periods of time up to and including 10 days. The microfluidic devices can be made from porous hydrophilic substrate, e.g. hydrophilic paper substrates. The devices can include a collection pad, an evaporative pump, and a channel connecting the collection pad and the evaporative pump. Hydrogels at the collection pad can promote collection of sweat or other biological fluids from a subject, which in some aspects is assisted by the use of one or more microneedles on the
(Continued)

Skin     Hydrogel Disc     Paper Strip          Evaporation Pad substrate. An evaporative pump can provide for long periods of sampling by providing continual pumping, e.g. through the use of an evaporation pad where sampled fluid can evaporate.

17 Claims, 28 Drawing Sheets

(51) Int. Cl.
    *A61B 5/15*           (2006.01)
    *B01L 3/00*           (2006.01)
    *A61B 5/00*           (2006.01)

(52) U.S. Cl.
    CPC .... *A61B 5/14532* (2013.01); *A61B 5/150061* (2013.01); *A61B 5/150969* (2013.01); *A61B 5/150984* (2013.01); *A61B 10/0051* (2013.01); *B01L 3/502707* (2013.01); *B01L 3/50273* (2013.01); *A61B 5/145* (2013.01); *A61B 5/15* (2013.01); *A61B 5/42* (2013.01); *A61B 10/0045* (2013.01); *A61B 2010/008* (2013.01); *A61B 2562/164* (2013.01); *B01L 2300/0816* (2013.01); *B01L 2300/126* (2013.01); *B01L 2300/161* (2013.01); *B01L 2400/0406* (2013.01); *B01L 2400/0466* (2013.01)

(58) Field of Classification Search
    CPC ........ A61B 5/150969; A61B 5/150984; A61B 10/0051; A61B 5/145; A61B 10/0045; A61B 2010/008; A61B 2562/164; A61B 5/150022; A61B 5/150099; A61B 5/150229; A61B 5/155; A61B 5/15; A61B 5/42; B01L 3/502707; B01L 3/50273; B01L 2300/0816; B01L 2300/126; B01L 2300/161; B01L 2400/0406; B01L 2400/0466; B01L 2300/123; B01L 2300/166; B01L 2200/0678

See application file for complete search history.

(56) References Cited

U.S. PATENT DOCUMENTS

| | | | |
|---|---|---|---|
| 2009/0312614 A1* | 12/2009 | Brenneman | A61B 5/6833 |
| | | | 600/309 |
| 2011/0111517 A1 | 5/2011 | Siegel et al. | |
| 2015/0132742 A1* | 5/2015 | Thuo | B01L 3/502707 |
| | | | 436/71 |
| 2018/0199866 A1* | 7/2018 | Heikenfeld | A61B 5/14521 |
| 2018/0345288 A1* | 12/2018 | Belotserkovsky | F04B 19/006 |

OTHER PUBLICATIONS

Nie, Chuan et al. "A microfluidic device based on an evaporation-driven micropump." Biomed Microdevices, 2015, vol. 17, article No. 47, internal pp. 1-12.

* cited by examiner

Hydrogel Preparation
* Polymerized and swell in NaCl solution
* Lasercut discs for testing Microfluidic Device Fabrication
* Polymerize PDMS on silicon wafer master mold
* Punch openings and use plasma treatment to bond pieces Test Setup Hydrogel Disc Dialysis Membrane Clamp onto device Fill chamber
with desired
solution $$Q = lw \, \frac{x_{i+1} - x_i}{t_{i+1} - t_i}$$

HYDROGEL-ENABLED MICROFLUIDIC SWEAT SEQUESTERING FOR WEARABLE HUMAN-DEVICE INTERFACES

CROSS-REFERENCE TO RELATED APPLICATION

This application is the 35 U.S.C. § 371 national stage application of PCT Application No. PCT/US2018/035761, filed Jun. 2, 2018, which claims priority to, and the benefit of, U.S. provisional application entitled "HYDROGEL-ENABLED MICROFLUIDIC SWEAT SEQUESTERING FOR WEARABLE HUMAN-DEVICE INTERFACES" having Ser. No. 62/514,232, filed Jun. 2, 2017, both of which are hereby incorporated by reference in their entireties.

STATEMENT REGARDING FEDERALLY SPONSORED RESEARCH OR DEVELOPMENT

This invention was made with government support under grant number 1160483 awarded by the National Science Foundation. The government has certain rights to this invention.

TECHNICAL FIELD

The present disclosure generally relates to microfluidic devices and uses thereof.

BACKGROUND

Wearable health monitors and activity monitors are among the most popular technology trends. Most of these devices utilize accelerometers and gyroscopes to obtain data on motion of the user and correlate that to physical activity. While these devices are great at tracking activity, patient health can only be inferred based off of movements. To obtain a very clear picture of a person's health, a biochemical test is usually performed. These tests are often performed on blood that has been drawn using a needle and then tested in a lab for various analytes. Blood sampling is invasive and very uncomfortable for the patient. Blood is not the only body fluid which can provide useful insight into the body's biochemical health. Sweat is a body fluid which is constantly released through the sweat glands. Sweat contains useful biochemical indicators such as glucose, lactate, cortisol and various ionic species.

There remains a need for improved devices for analyzing analytes in sweat and other fluids that overcome the aforementioned deficiencies.

SUMMARY

Microfluidic devices and methods of using microfluidic devices are provided that overcome one or more of the aforementioned deficiencies. In various aspects, microfluidic devices are provided having a porous hydrophilic substrate having both an upper surface and a lower surface, the porous hydrophilic substrate having a reservoir/collection pad, an evaporative pump, and a channel, connecting the collection pad and the evaporative pump. In various aspects, a hydrogel is on the upper surface of the porous hydrophilic substrate at the collection pad, wherein the hydrogel includes a plurality of extractants. Extractants can include, for example, various salts or other solutes to create an osmotic pressure difference for pulling fluid into the hydrophilic substrate. The porous hydrophilic substrate can have a thickness of about 0.05 mm to 0.5 mm. The device can include one or more sensors such as optical sensors, electrochemical sensors, fluorescent sensors, colorimetric sensors, turbidimetric sensors, or a combination thereof, at a location along the channel. The sensors can provide monitoring of one or more analytes in a fluid in the channel.

In various embodiments, the porous hydrophilic substrate include a cellulosic substrate. Suitable cellulosic substrates can include, for example, paper, cellulose derivatives, woven cellulosic materials, and non-woven cellulosic materials. Paper can include chromatography paper, card stock, filter paper, vellum paper, printing paper, wrapping paper, ledger paper, bank paper, bond paper, blotting paper, drawing paper, fish paper, tissue paper, paper towel, wax paper, or photography paper. Various weight papers can be used, for example paper having a grammage of about 0.5 g/m$^2$ or more. Synthetic "non-woven" paper-like materials can be used as substitutes for natural material papers.

The collection pad can have various dimensions suitable for the application needs. In some aspects, the collection pad has a surface area from about 1 mm$^2$ to 100 mm$^2$. The collection pad can be connected on one end to the channel, which can have a variety of dimensions. In some aspects, the channel has a width of about 100 μm to 1000 μm, a height of about 50 μm to 500 μm, a length of about 1 mm to 20 mm, or any combination thereof. A variety of channels can be used in various aspects described herein. In some aspects, the channel is a thin strip of paper or other porous hydrophilic material that connects the collection pad and the evaporative pump. In some aspects, the channel is a hydrophilic conduit in a paper or other hydrophobic substrate. For example, a paper or other porous substrate may include hydrophobic portions and one or more hydrophilic portions defining a conduit through the paper or other hydrophobic substrate.

The device can include an evaporative pump to create a driving force for pumping a fluid through the channel. In some embodiments, the evaporative pump includes a paper or other evaporation pad having a surface area of about 0.1 cm$^2$ to 10 cm$^2$. In some aspects, the evaporative pump has a surface area of about 0.1 cm$^2$ to about $A_{max}$, wherein $A_{max}$ is calculated according to the following formula $$A_{max} = \left( \frac{\Delta P h \kappa \rho}{\mu L H} \right) w$$

where ρ is a density of a fluid, L is a length of the channel, h is height of the channel, w is a width of the channel, μ is a viscosity of the fluid flowing through the channel, κ is a permeability of the fluid flowing through the channel, ΔP is a pressure drop over the length of the channel, and H is an evaporation flux of the evaporation pad. In some aspects, the evaporative pump has a semicircular evaporation pad extending radially from an end of the channel.

The hydrogel can be any size as required by the size of the microfluidic device. In some aspects, the hydrogel has a cross-sectional surface area of about 1 mm$^2$ to 100 mm$^2$, a thickness of about 1 mm to 10 mm, or a combination thereof. In some aspects, a variety of hydrogels can be used with the devices. In some aspects, the hydrogel includes a cross-linked network of one or more hydrophilic polymers. The hydrogel can include a polyacrylate, a polyurethane, a silicone, an agarose, a collagen, an alginate, copolymers thereof, and blends thereof. The hydrogel can include a copolymer of an acrylate or an acrylamide crosslinker and a second monomer such as N-vinyl pyrrolidone, an N-vinyl lactam, an acrylamide, a urethane, or a combination thereof. The hydrogel can include a polymer selected from the group consisting of a poly (lactide-co-glycolide), a polyacrylamide, a polyurethane, a polyacrylonitrile, a poloxamer, an N-Isopropylacrylamide copolymer, a poly(N-isopropylacrylamide), a poly(vinyl methyl ether), a PEGylated copolymer thereof, a copolymer thereof, and a blend thereof; wherein the polymer is crosslinked by an acrylate or an acrylamide crosslinker. In some aspects, the hydrogel is an acrylamide monomer that has been crosslinked by an n,n'-methylenebisacrylamide crosslinker.

The hydrogel can include a plurality of extractants to create an osmotic driving force to pull the fluid into the device. The extractants, in some aspects, can be present in the hydrogel at a total concentration of about 0.15 M to 20 M. The extractants can include salts such as NaCl, KCl, $CaCl_2$, $NH_4Cl$, or a combination thereof. The extractants can include organic extractants such as a polyols, e.g. ethylene glycol, propylene glycol, glycerol, other organic oils, or a combination thereof.

The microfluidic devices provided can be used with a variety of fluids. The fluid can include a hydrophilic fluid. Suitable fluids can include, but are not limited to, water, blood, urine, saliva, sweat, tissue exudate, tissue transudate, and a combination thereof. Methods of measuring an analyte in a fluid are also provided. The methods can include using one of the microfluidic devices provided herein.

In various embodiments, the methods include placing the lower surface of a microfluidic device described herein above the fluid, and measuring the analyte in the fluid by detecting the analyte with a sensor as it passes through the channel in the microfluidic device. For example, the methods can include placing the microfluidic device on the skin of a subject such as a mammal, e.g. a human. In various aspects, the hydrogel has a higher osmotic pressure than the osmotic pressure of the fluid below the lower surface. The extractants in the hydrogel can create an osmotic driving force pulling the fluid into the collection pad of the microfluidic device. The evaporative pump can allow the fluid to evaporate after passing through the channel, creating a capillary driving force to pump the fluid through the channel. The evaporative pump can include an evaporation pad, and the fluid can evaporate from the evaporation pad after passing through the channel, creating a capillary driving force to pump the fluid through the channel. In some aspects, the fluid can be continually pumped through the channel for a period of time from about 5 hours or 10 hours and up to about 5 days or 10 days. In various aspects, the fluid can be pumped through the channel at a linear flow rate of about 0.1 mm/min to 10 mm/min. The methods can be used for analyzing a variety of analytes such as glucose, uric acid, lactic acid, cortisol, nitrates, cholesterol, or a combination thereof.

Other systems, methods, features, and advantages of microfluidic devices and uses thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 7A is a series of fluorescent microscope images of the microfluidic channel over time as the fluorescent of the flow increases. FIG. 7B is a calibration curve created to correlate the fluorescent intensity to a relative concentration with 100% being equal to what is in the chamber below the membrane. FIG. 7C depicts how the calibration curve from FIG. 7B was used to then determine how representable the fluid flowing through the channel was to the fluid in the chamber (C).

FIG. 9A is a perspective view of the exemplary microfluidic device. FIG. 9B is an exploded view of the exemplary microfluidic device. FIG. 9C is a side view of the exemplary microfluidic device when placed on a skin surface for continual sampling of sweat or other bodily fluids from below the skin surface.

FIG. 10A depicts the exemplary hydrogel based microfluidic pumping platform, with a hydrogel disc that interfaces the body, where it passively pumps sweat and passes it to an adjacent microfluidic network that has an embedded biosensor. FIG. 10B is an image of fluorescent particles showing the pumping of the fluid through the membrane towards the microchannel. FIGS. 10C-10F demonstrate that the hydrogel pumping rate increases with increased osmotic pressure (FIG. 10C) and hydrogel surface area (FIG. 10D), while hydrogel thickness has no effect on pumping rate (FIG. 10E). FIG. 10F is a graph showing measurement of glucose that was pumped through the exemplary device using a commercial glucose sensor for diabetic testing. The solution being pumped contained 50 mg/dL glucose, a biologically relevant amount, and was measured accurately at the end of the microfluidic channel.

Figure 11A:
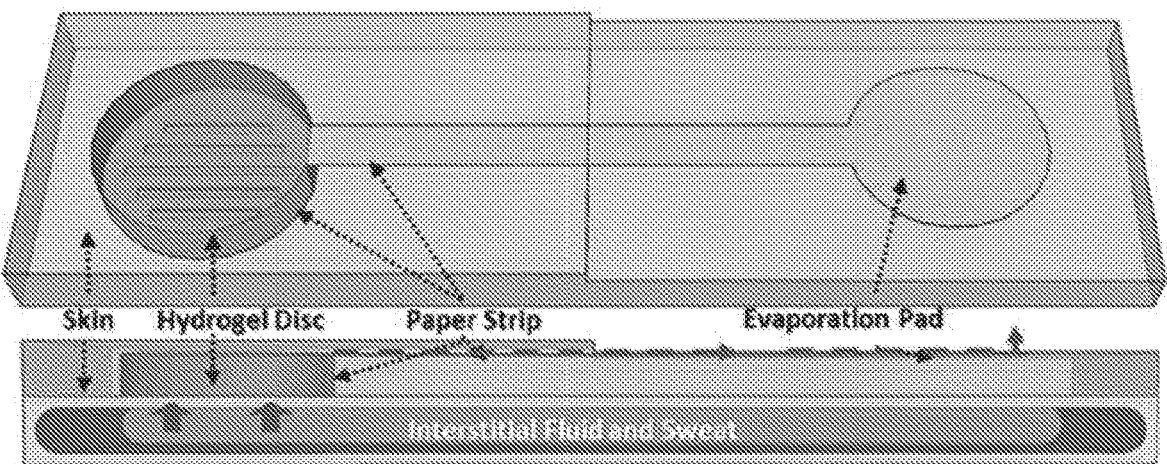
Figure 11B:
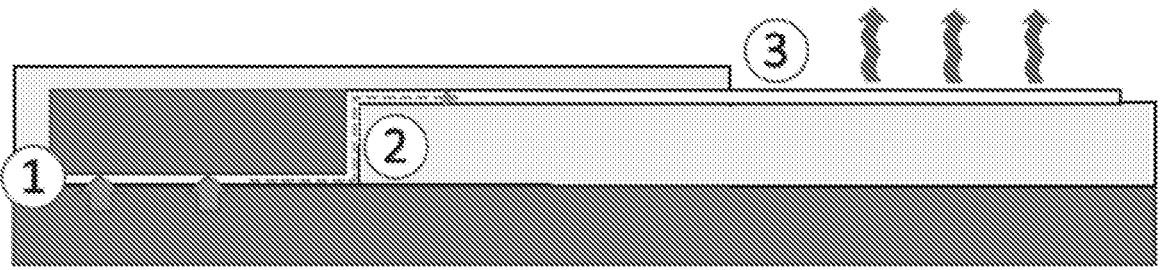

FIGS. 11A-11B depict an exemplary embodiment of a microfluidic device for continual sampling of interstitial fluid and sweat. FIG. 11A includes a perspective view (top) and a side view (bottom) of the exemplary microfluidic device. FIG. 11B depicts a side view of the exemplary microfluidic device of FIG. 11A, depicting three mechanisms operating within the exemplary device including (1) the hydrogel draws sweat from the body due to the osmotic pressure gradient, (2) a paper microfluidic strip that interfaces both the skin and hydrogel draws the pumped fluid via capillary wicking, and (3) Sweat evaporates off the evaporation pad to allow for more sweat to be continually wicked from the skin by the paper channel.

Figure 12A:
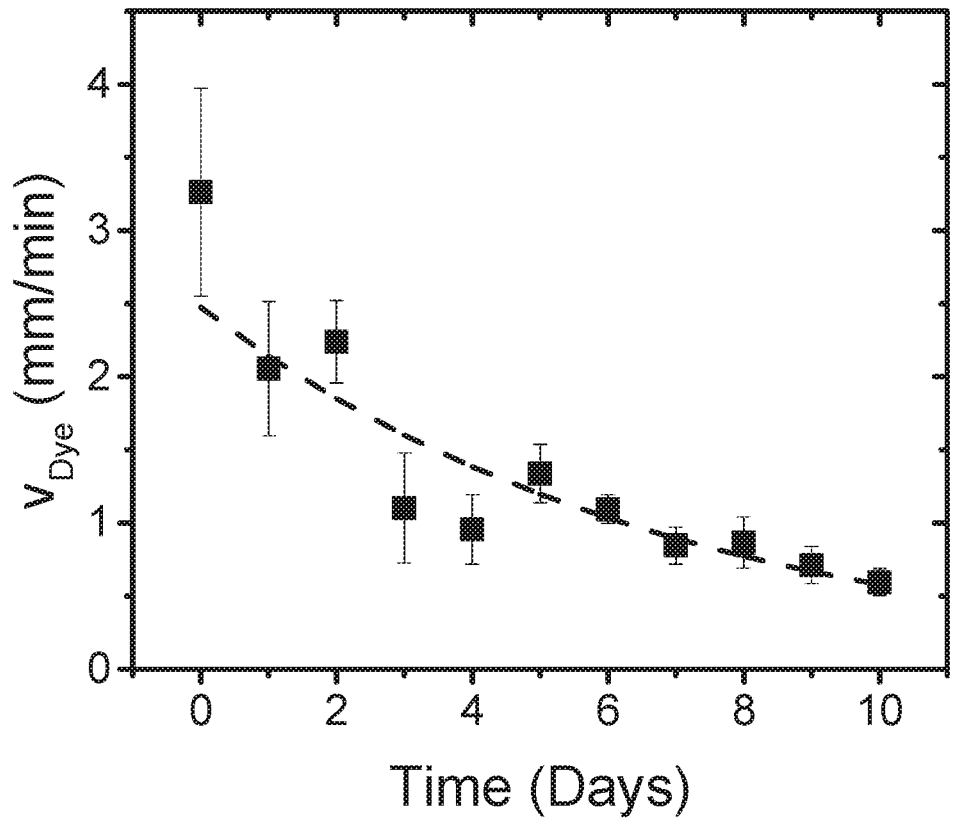
Figure 12B:
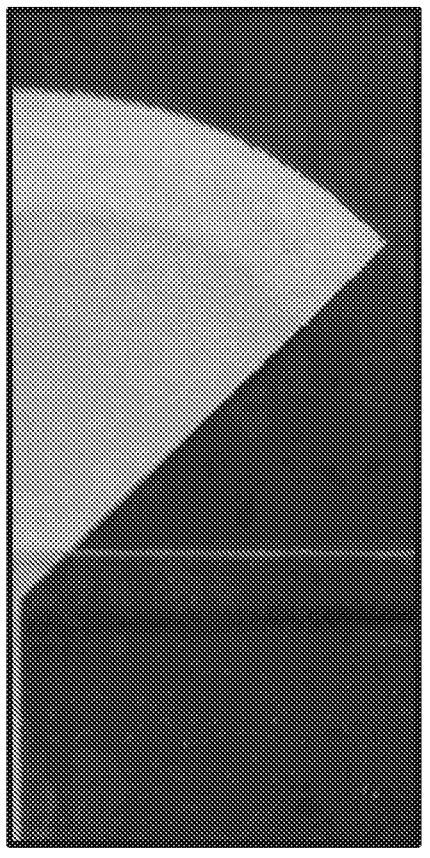

FIGS. 12A-12B demonstrate long-term performance of an exemplary paper microfluidic device with a sweat simulant. FIG. 12A is a graph showing the velocity of a dye being pumped by evaporation through a paper microfluidic device over the span of 10 days. FIG. 12B is an image showing an example of salt accumulation in a real device, which nevertheless continues working until all evaporation patch is covered with salt layer.

Figure 13A:
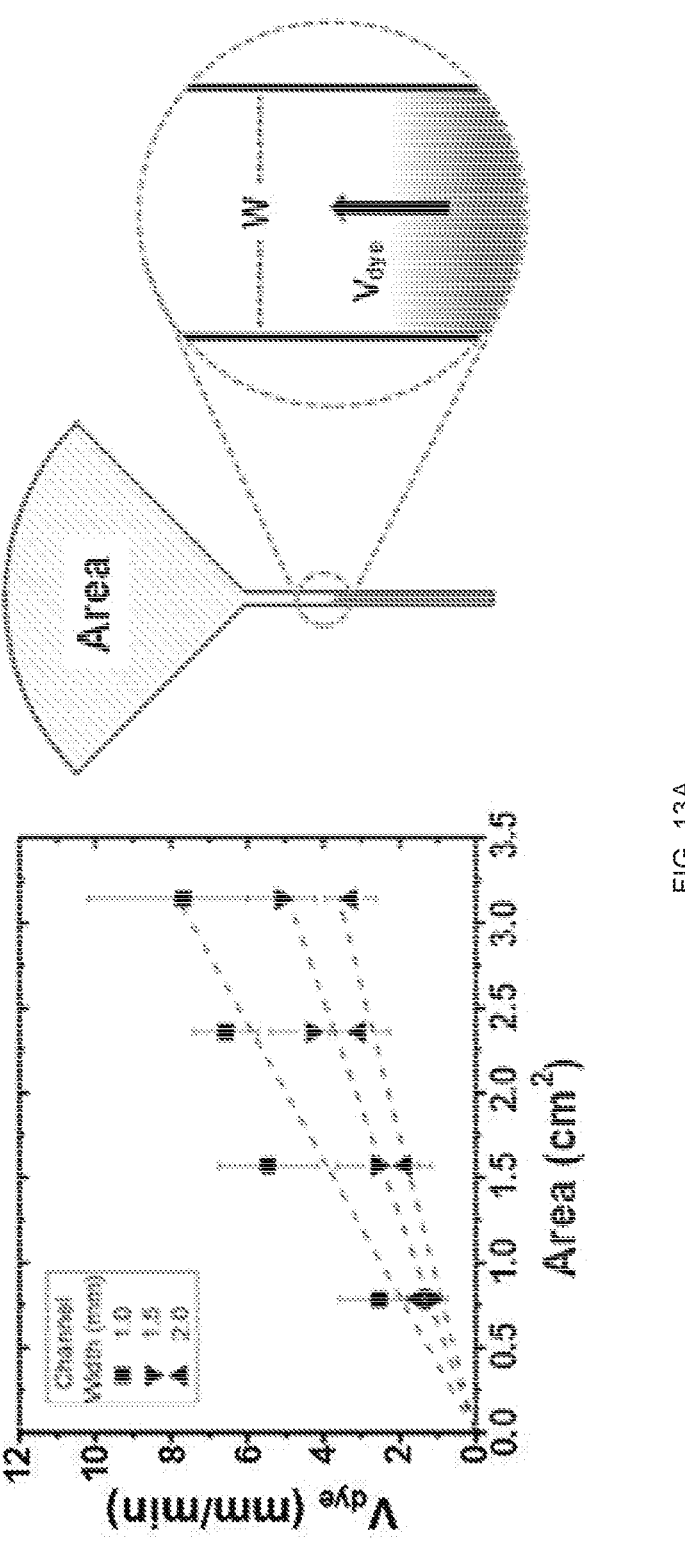
Figure 13B:
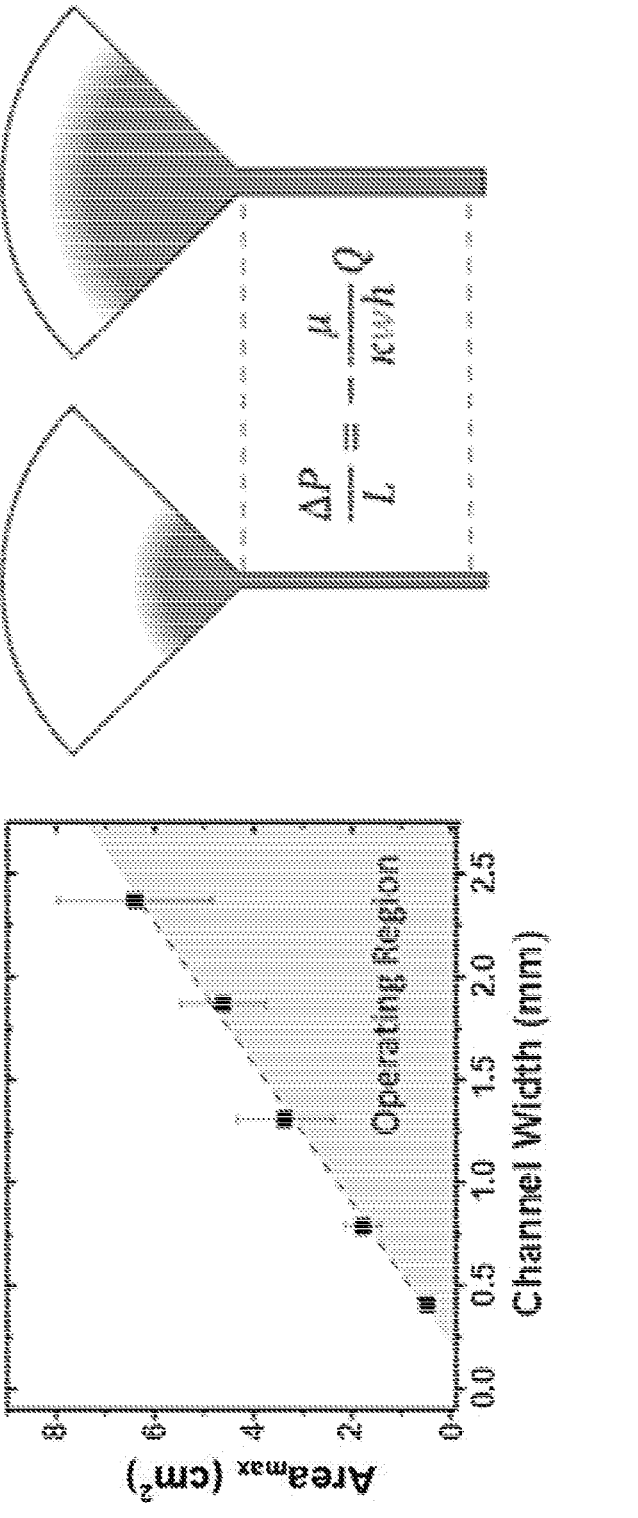

FIG. 13A is a plot of the measured dye velocity in the paper channel relative to the size of the evaporation pad for various widths of channels. FIG. 13B is a plot showing the maximum wetting area achieved on the evaporation pad vs. the channel width.

Figure 14A:
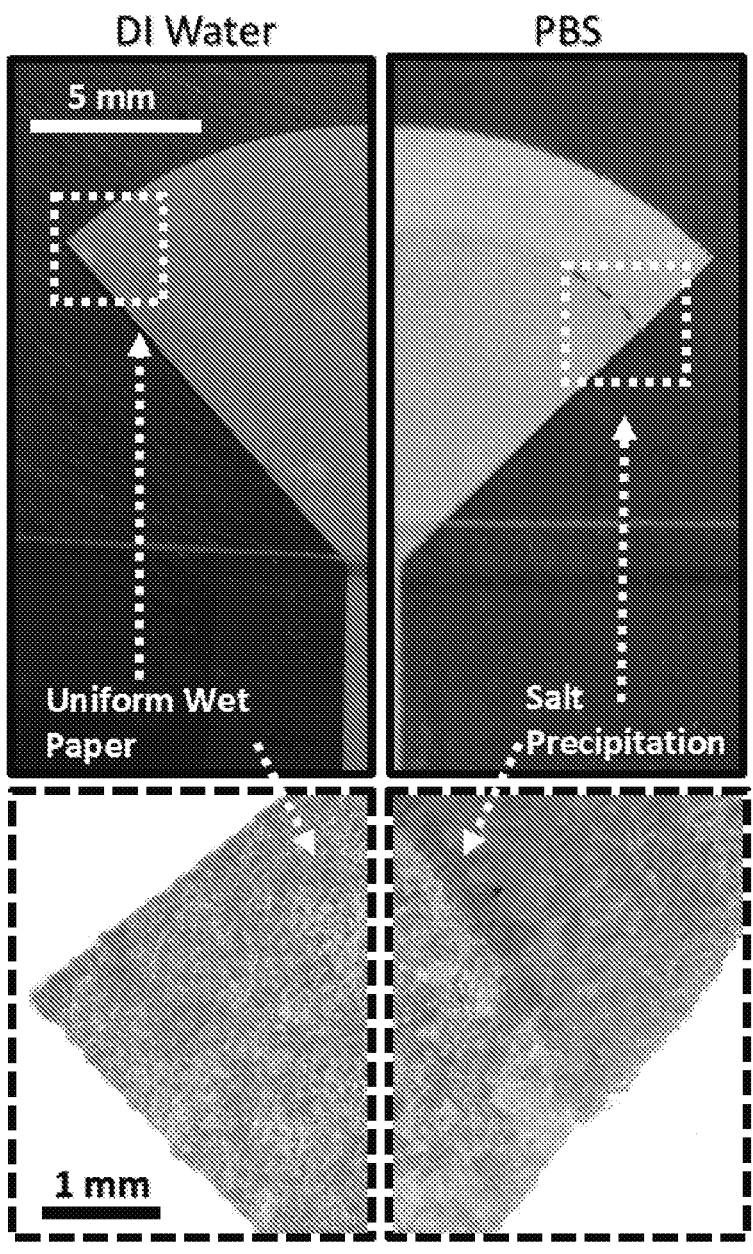
Figure 14B:
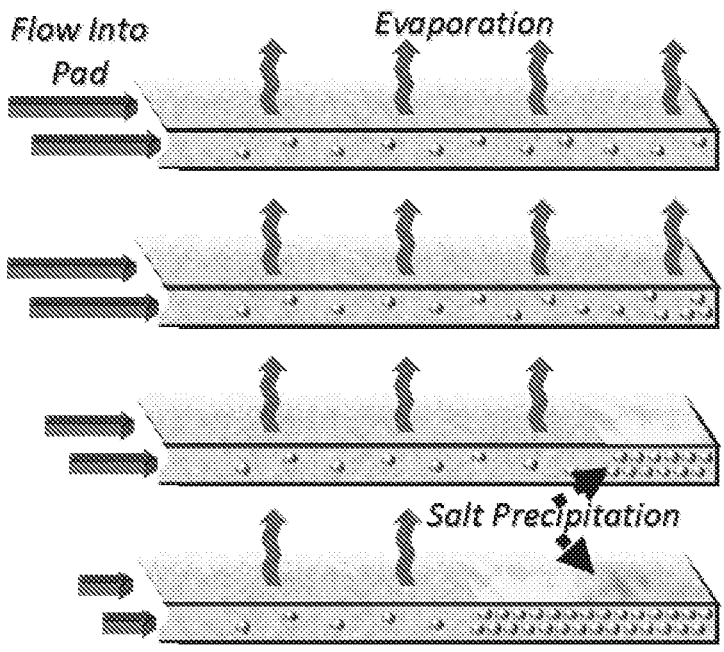
Figure 14C:
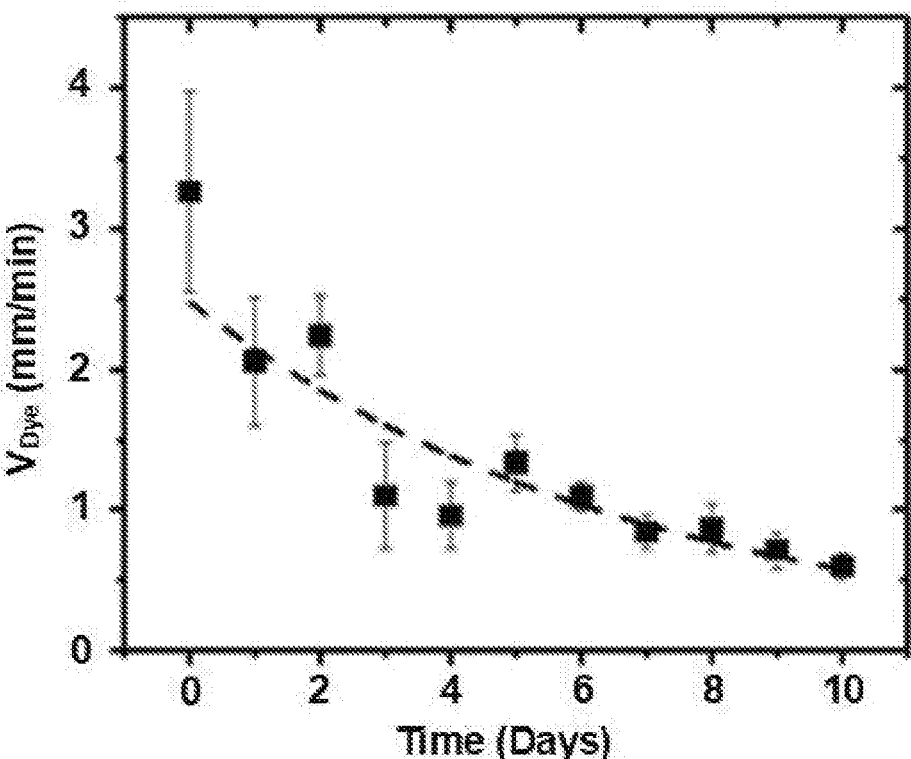
Figure 14D:
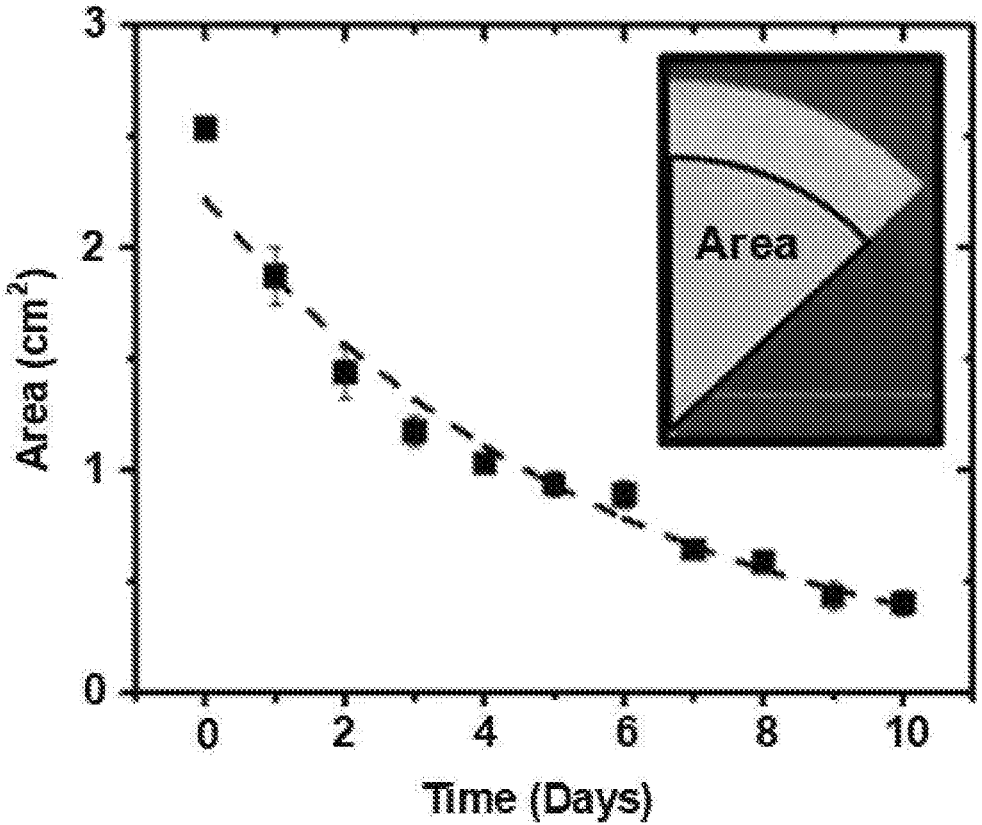
Figure 14E:
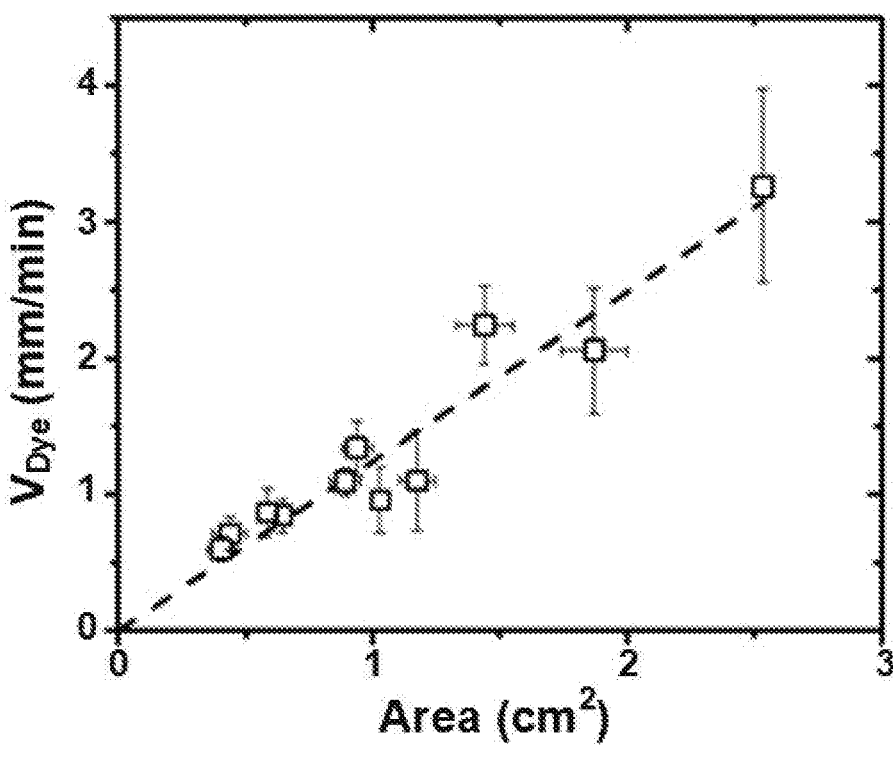

FIG. 14A is a series of images and micrographs showing the evaporating pad of the paper strip under operation of DI water and PBS. With PBS, salt accumulates at the periphery of the pad over time, where DI water results in a homogenous paper substrate. FIG. 14B is a schematic showing the mechanism of salt accumulation. Salt concentration first builds up at the edge of the strip as water evaporates. Excess salt begins to precipitate along the edge, resulting in a front of salt crystals moving inward from the edge of the pad. FIG. 14C is a plot of the velocity of a fluorescent dye measured over a 10-day span to determine the effect of salt accumulation on fluid flow. FIG. 14D is a graph of the area of the paper pad not covered by salt crystals as measured over this span. Both velocity and area show a negative exponential decay over time. FIG. 14E is a graph of the velocity plotted vs. area remaining with a linear trend.

Figure 15A:
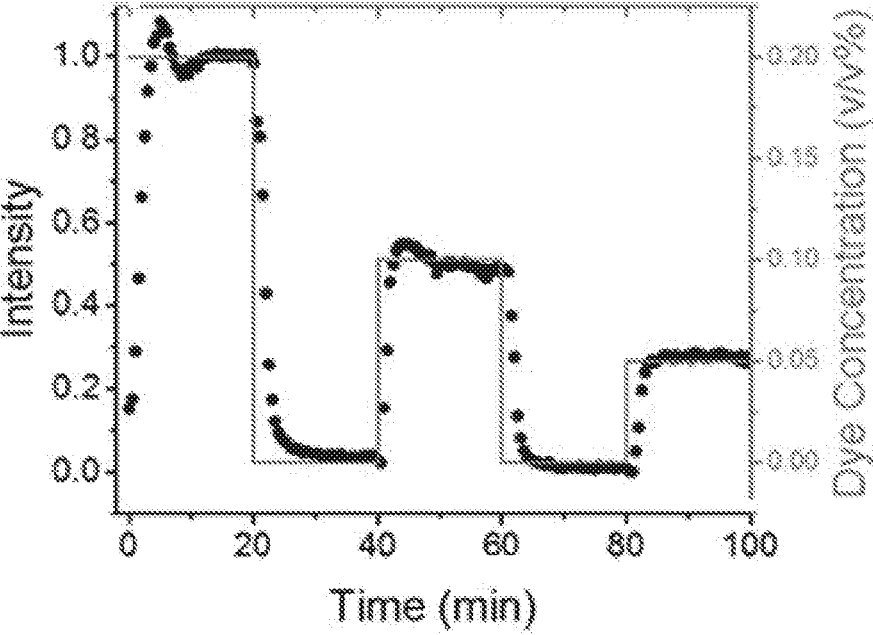
Figure 15B:
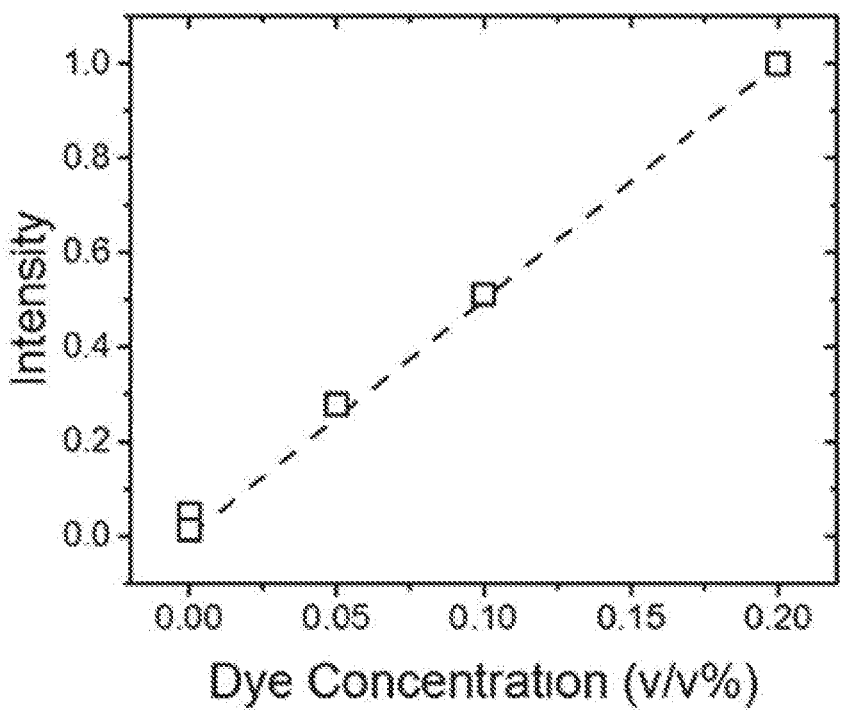
Figure 15C:
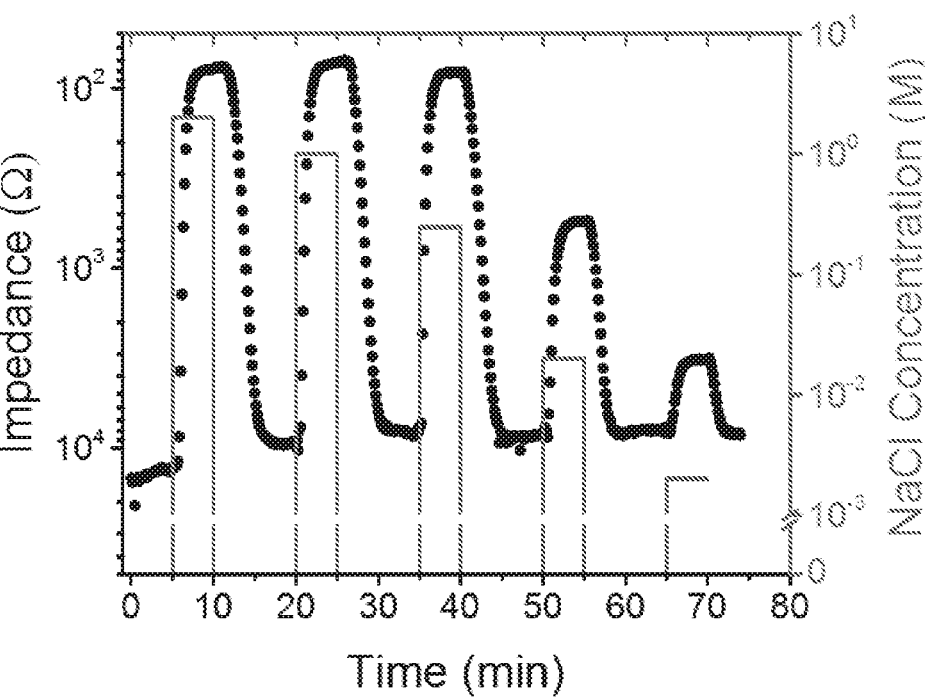
Figure 15D:
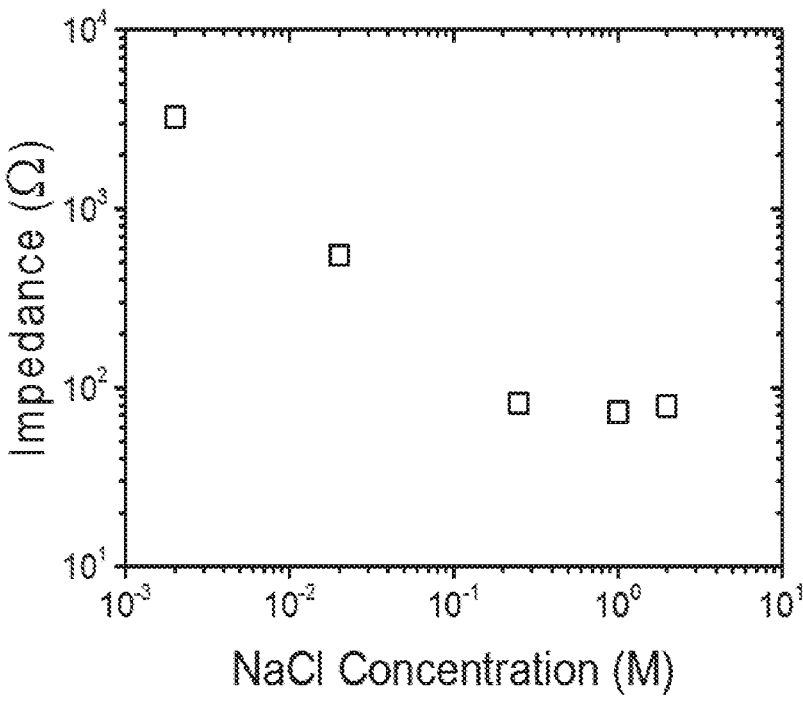

FIG. 15A is a plot showing measured intensity in a paper channel while the concentration of dye in the solution being sampled was adjusted via step changes. FIG. 15B is a graph of intensity plotted vs. dye concentration demonstrates the expected linear concentration. FIG. 15C is a plot of electrical sensing during continual evaporative pumping. Impedance at 1 MHz was measured using a gold interdigitated electrode interfaced to the paper strip. The impedance was monitored over time as the sensing solution was varied between saline solutions ranging from 0.002 to 2 M with DI water intermittently (note that impedance was plotted inversely on the y axis). FIG. 15D is a plot of impedance vs. salt concentration. An inverse relationship can be seen up to 0.2 M, at which point interface and electrode resistances were dominant and led to a leveling of impedance. These plots show the ability of this pumping mechanism to work for both electrical and colorimetric sensing applications.

DETAILED DESCRIPTION

In various aspects, microfluidic devices and methods of use are provided, for example for interfacing the skin of a human or non-human mammal. The microfluidic devices and methods of use can, in some embodiments, be used for non-invasive biochemical sensing through continual sweat sequestering using hydrogel osmotic pumping. In some embodiments, the microfluidic devices utilize a hydrogel based passive fluid pump to pump sweat during periods of low sweat in humans. In some aspects, the devices and methods can be used for continual biochemical monitoring of glucose and lactate in sweat or interstitial fluid. The microfluidic devices in some aspects combine paper microfluidics with osmotically doped hydrogel to (1) utilize the porous capillary structure of the paper to wick sweat past an embedded sensor during periods of high sweat rate and (2) allow for the doped hydrogels to passively pump sweat during periods of low sweat rate. Using paper microfluidics and hydrogel osmotic pumping, the devices can be highly cost-effective and practically usable for disposable applications.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "microfluidic device," as used herein, refers to a device that includes one or more microfluidic channels, fluidic transport paper strips, one or more microfluidic chambers, one or more micro-wells, or combinations thereof designed to carry, store, mix, react, and/or analyze liquid samples, typically in volumes of less than one milliliter.

The term "microfluidic channel," as used herein, refers to a feature within a microfluidic device that forms a path, such as a conduit, through which one or more fluids can flow. Microfluidic channels can have at least one cross-sectional dimension that is in the range from about 0.1 microns to about 1000 microns. Microfluidic channels can include open channels, closed channels, or both open and closed channels. Microfluidic channels can also be made of porous paper or other material transmitting directionally the fluid.

The term "substrate," as used herein, refers to a material that forms the structural components of a microfluidic device and in which the microfluidic channels, microfluidic chambers, and/or the micro-wells are formed.

The term "open channel," as used herein, refers to a microfluidic channel that includes a central void space through which a liquid sample flows, and a bottom and side walls formed from a substrate such fluid flows through the open channel.

The term "closed channel," as used herein, refers to a microfluidic channel that includes a porous hydrophilic substrate through which fluid flows by wicking.

The term "paper," as used herein, refers to a web of cellulosic fibers that are formed, for example, from an aqueous suspension on a wire or screen, and are held together at least in part by hydrogen bonding. Papers can be manufactured by hand or by machine. Paper can be formed from a wide range of matted or felted webs of vegetable fiber, such as "tree paper" manufactured from wood pulp derived from trees, as well as "plant papers" or "vegetable papers" which include a wide variety of plant fibers (also known as "secondary fibers"), such as straw, bamboo, flax, and rice fibers. Paper can be formed from substantially all virgin pulp fibers, substantially all recycled pulp fibers, or both virgin and recycled pulp fibers. Paper can also materials generally referred to as "nonwovens". Paper can also include adhesives, fillers, dyes, and other additives.

The term "flexible," as used herein, refers to a property of a pliable material in that it can be substantially bent through its thinnest dimension and return to a flat configuration without damaging the integrity of the material.

The term "hydrophilic," as used herein, refers to the property of having affinity for water. As a result, hydrophilic surfaces have a tendency to absorb water and/or be wetted by water. In certain embodiments, hydrophilic surfaces or substrates have a water contact angle of less than 90°.

The term "hydrophobic," as used herein, refers to the property of having a lack of affinity for, or even repelling water. As a result, hydrophobic surfaces have a tendency not to be wetted by water. In certain embodiments, hydrophobic surfaces or substrates have a water contact angle of greater than 90°.

The term "extractant," as used herein, refers to substances with high water solubility that acts to increase the osmotic pressure of water when dissolved in an aqueous solution or a hydrogel containing aqueous solution. The extractant can be nonvolatile or volatile. In some aspects, the extractant is nontoxic and non-irritating to skin.

Microfluidic Devices

In various embodiments, microfluidic devices are provided. The microfluidic devices can include a porous hydrophilic substrate having both an upper surface and a lower surface, the porous hydrophilic substrate including a collection pad, an evaporative pump, and a channel connecting the collection pad and the evaporative pump; and a hydrogel on the upper surface of the porous hydrophilic substrate at the collection pad, wherein the hydrogel contains a plurality of extractants.

The microfluidic device can include a variety of channels. The channels can include open channels. The channels can include a thin strip of paper or other porous hydrophilic material that connects the collection pad and the evaporative pump. In some aspects, the channel is a hydrophilic conduit in a paper or other hydrophobic substrate. For example, a paper or other porous substrate may include hydrophobic portions and one or more hydrophilic portions defining a conduit through the paper or other hydrophobic substrate. In some aspects, the channel and the evaporative pump are formed from a single thin strip of paper or other porous hydrophilic material. For example, a paper or other porous hydrophilic material can be cut or shaped to form both the channel and the evaporative pump. In some aspects, a paper or other porous substrate may include hydrophobic portions and one or more hydrophilic portions defining the channel and the evaporative pump.

The substrate can contain a variety of additional microfluidic components, such as additional microfluidic channels, paper coatings or strips, microfluidic chambers, microwells, or combinations thereof designed to carry, store, mix, react, and/or analyze liquid samples, typically in volumes of less than one milliliter. Additional elements can also include valves, fluid inlets, and combinations thereof, so as to permit the efficient handling of fluids.

The microfluidic devices can include at least one fluid flow path, formed by one or more microfluidic components through which fluid flows during sample processing. The microfluidic device can include at least one collection pad and at least one evaporative pump connected by one or more microfluidic channels such that, under operating conditions, fluid flows from the collection pad through the one or more channels and into the evaporative pump. In some cases, a single microfluidic device can include multiple fluid flow paths or channels. In these instances, the plurality of channels may be positioned in any convenient arrangement within the device, and may or may not intersect, depending on the device design.

As described herein, microfluidic devices can include multiple microfluidic channels, which intersect at various points. In some cases, two or more microfluidic channels converge into a single microfluidic channel. Such a design can be incorporated into a microfluidic device, for example, to combine two or more liquids within a microfluidic device. Similarly, two or more microfluidic channels can diverge from a single microfluidic channel, so as to, for example, permit a sample to be separated into multiple flow paths that can be independently analyzed. Microfluidic channels can intersect and diverge in a variety of fashions as required for device performance, including Y-shaped intersections, T-shaped intersections, and crosses. In addition, a plurality of microfluidic channels can converge in or diverge from a microfluidic chamber or collection pad. In some aspects, a device can include multiple channels each terminating with an evaporative pump to allow for different analytes to be analyzed in each channel. In some aspects, one or more of the channels may be combined with a separate channel including a reactant to be used in analyzing or detecting the analyte. So, in some embodiments, the microfluidic device can include more than one collection pad, for example one collection pad containing the hydrogel above and a second collection pad including a source of reactant.

A variety of substrates can be useful in the microfluidic devices described herein. The substrate can include a cellulosic substrate as part or a whole of a channel or evaporating pad. Generally, the cellulosic substrate is flexible. In preferred embodiments, the cellulosic substrate can be bent through its thinnest dimension, rolled around a cylindrical rod with a diameter of at least two inches, and return to a flat configuration without damaging the integrity of the substrate, such that a microfluidic device fabricated from the cellulosic substrate can be treated in this fashion without damaging the integrity and/or functionality of the microfluidic device. For certain applications, it is preferable that the cellulosic substrate can be folded, creased, or otherwise mechanically shaped to impart structure and function to a microfluidic device formed from the cellulosic substrate. In some aspects, the porous hydrophilic substrate has a thickness of about 0.01 mm to 1 mm, about 0.01 mm to 0.5 mm, about 0.05 mm to 0.5 mm, about 0.05 mm to 0.3 mm, or about 0.1 mm to 0.3 mm.

Examples of suitable substrates include cellulose; derivatives of cellulose such as nitrocellulose or cellulose acetate; paper (e.g., craft paper, card stock, filter paper, chromatography paper); woven cellulosic materials; non-woven cellulosic materials; and thin films of wood.

Preferably, the cellulosic substrate is paper. Paper is inexpensive, widely available, readily patterned, thin, lightweight, and can be disposed of with minimal environmental impact. Furthermore, a variety of grades of paper are available, permitting the selection of a paper substrate with the weight (i.e., grammage), thickness and/or rigidity and surface characteristics, desired for the fabrication of a particular microfluidic device. Suitable papers can include, but are not limited to, chromatography paper, card stock, filter paper, vellum paper, printing paper, wrapping paper, ledger paper, bank paper, bond paper, blotting paper, drawing paper, fish paper, tissue paper, paper towel, wax paper, and photography paper. The paper can include cardstock paper, which is particularly suitable as the cellulosic material is lightweight and flexible, sufficiently smooth to create a tight seal with tape and inexpensive; it is also thick enough (300 μm) to retain mechanical stability while accommodating the channel depths generated using etching or carving. Thinner, more flexible paper, or artificial nonwovens can be used when channels are introduced into the paper by embossing, if desired. In some aspects, the paper is a filter paper or similarly dimensioned paper that can be used, for example, to form all or part of a channel, or to form all or part of an evaporation pad, or form all or part of both a channel and an evaporation pad.

In certain embodiments, the cellulosic substrate is paper having a grammage, expressed in terms of grams per square meter ($g/m^2$), of about 50, 60, 70, 75, 85, 100, 125, 150, 175, 200, 225, 250, or greater.

The substrate includes one or more microfluidic channels. The channels can be linear in shape, or they can have any other configuration required for device function, including a curved configuration, spiral configuration, angular configuration, or combinations thereof. The channels can range in length from about 100 μm to about 50 mm, about 100 μm to 30 mm, about 1 mm to 30 mm, about 5 mm to 30 mm, or about 10 mm to 20 mm. The channels can be open channels, closed channels, or thin strips of paper or other porous hydrophilic material channels. In some aspects, the microfluidic device can include all open channels, all closed channels, all paper channels, or a combination thereof. The channels can have a width, measured as the distance between the two side walls of the microfluidic channel at the surface of the cellulosic substrate, of about 10 μm to 1000 μm, about 100 μm to 1000 μm, about 100 μm to 500 μm, about 100 μm to 300 μm. In some aspects, channels are dimensioned or configured such that fluid is capable of flowing or wicking through the channel by capillary flow (i.e., the channel is of capillary dimensions or includes capillary wicking in paper). By capillary dimensions, it is meant that the width of the channel does not exceed about 1000 μm, e.g. about 750 μm to 1000 μm, about 500 μm to 750 μm, about 250 μm to 500 μm, about 10 to 250 μm, or about 50 to 70 μm. The channels will generally have a height less than the thickness of the substrate. In some aspects, the channels have a height of about 50 μm to 500 μm.

The substrate can include one or more collection pads. Collection pads include, for example, depressions, chambers, or hydrophilic mats formed within the substrate that can hold a solid or liquid sample. In certain embodiments, the substrate device includes a plurality of collection pads. The substrate can include one or more collection pads in combination with one or more channels. In some aspects, the collection pad has a surface area, measured as the cross-sectional area of the collection pad measured in the plane of the substrate, of about 1 mm$^2$ to 1000 mm$^2$, about 10 mm$^2$ to 1000 mm$^2$, about 10 mm$^2$ to 100 mm$^2$, or about 20 mm$^2$ to 100 mm$^2$.

The substrate can include one or more evaporative pumps, typically made of paper or porous hydrophilic material. An evaporative pump allows for and/or promotes the evaporations of the fluid in order to create a capillary driving force to continually pump the fluid through the channel. The evaporative pump can include an evaporation pad having a surface area to promote evaporation of the fluid. The evaporative pump can include a semicircular evaporation pad extending radially from an end of the channel.

In some aspects, the surface area of the evaporation pad is about 0.01 cm$^2$ to 10 cm$^2$, about 0.1 cm$^2$ to 20 cm$^2$, about 1 cm$^2$ to 10 cm$^2$, or about 1 cm$^2$ to the maximal wettable surface area (A$_{max}$). In some aspects, the surface area of the evaporation pad is at least as large as the maximal wettable surface area (A$_{max}$). A$_{max}$ can be calculated according to the following formula $$A_{max} = \left( \frac{\Delta P h \kappa \rho}{\mu L H} \right) w$$

where $\rho$ is a density of a fluid, L is a length of the channel, h is height of the channel, w is a width of the channel, $\mu$ is a viscosity of the fluid flowing through the channel, $\kappa$ is a permeability of the fluid flowing through the channel, $\Delta P$ is a pressure drop over the length of the channel, and H is an evaporation flux of the evaporation pad. Suitable fluids can include water, blood, urine, saliva, sweat, tissue exudate, tissue transudate, or a combination thereof. In most aspects, the fluid is aqueous, meaning the solvent is at least 50% water. In some aspects, the fluid is a hydrophilic fluid. In some aspects, the fluid is soluble and/or miscible with water.

The microfluidic device can include a hydrogel on the upper surface of the porous hydrophilic substrate at the collection pad. The hydrogel can include a plurality of extractants. Extractants are provided to decrease the vapor pressure of the hydrogel so as to create an osmotic driving force, driving fluid from below the substrate into the collection pad.

Hydrogels are well known in the literature. The hydrogel can include a crosslinked network of one or more hydrophilic polymers. The hydrogel can include a polyurethane, a silicone, a polyolefin, a polychloroprene, a collagen, an alginate, copolymers thereof, and blends thereof. Hydrogels can be made by combining an acrylate or acrylamide crosslinker with suitable monomers and a suitable initiator. Crosslinkable monomers can an N-vinyl pyrrolidone, an N-vinyl lactam, an acrylamide, a urethane, or a combination thereof. Suitable hydrogels can be made by crosslinking certain crosslinkable polymers. Suitable polymers can include poly (lactide-co-glycolide), a polyacrylamide, a polyurethane, a polyacrylonitrile, a poloxamer, an N-Isopropylacrylamide copolymer, a poly(N-isopropylacrylamide), a poly(vinyl methyl ether), a PEGylated copolymer thereof, a copolymer thereof, or a blend thereof. The polymers can be crosslinked by an acrylate or acrylamide crosslinker. In certain aspects, the hydrogel is an acrylamide monomer that has been crosslinked by an n,n'-methylenebisacrylamide crosslinker.

The hydrogels can be prepared having a variety of dimensions suitable for the specific device and application. The hydrogel can have a cross-sectional surface area, measured as a cross-section area parallel with the plane of the substrate, of about 1 mm$^2$ to 100 mm$^2$. The hydrogel can have a thickness, measured as the width perpendicular to the plane of the substrate, of about 0.1 mm to 5 mm, about 3 mm to 7 mm, or about 1 mm to 20 mm.

A variety of extractants can be used in the hydrogels described herein. In preferred embodiments, the extractants are salts. The extractant can be present in the hydrogel at a total concentration of about 1 M To 20M. Suitable salts can include, but are certainly not limited to, NaCl, KCl, CaCl$_2$, NH$_4$Cl, and a combination thereof. In some aspects, an organic extractant can be used. Suitable organic extractants can be alone or can be used in combination with a salt. Organic extractants can include polyols such as ethylene glycol, propylene glycol, glycerol, various glucose and sugar derivatives and a combination thereof.

The microfluidic device can include one or more sensors and/or one or more assay regions. Assay regions can include one or more assay reagents that serve as indicators for the presence of one or more analytes. The one or more assay regions may also include a sensor or electrode assembly that can be used to detect or quantify one or more analytes within a liquid sample. Sensors can be located, for instance, at a point along the length of the channel. Sensors can include suitable optical sensors, electrochemical sensors, fluorescent sensors, impedance sensors, turbidimetric sensors, or a combination thereof. The sensors can include an electrode assembly. In these embodiments, the one or more electrodes can be fabricated from suitable conductive materials, including carbon ink, silver ink, Ag/AgCl ink, copper, nickel, tin, gold, platinum, and combinations thereof.

Suitable assay reagents can be included in the device to be used in conjunction with the sensors and/or electrode assemblies. Assay reagents can serve as indicators for the presence of one or more analytes. In certain embodiments, the assay reagents facilitate the detection and/or quantification of one or more analytes, such as small molecules, proteins, lipids, polysaccharides, nucleic acids, prokaryotic cells, eukaryotic cells, particles, viruses, fungi, metal ions, or combinations thereof.

In certain cases, the microfluidic devices can be intended to detect and/or quantify one or more analytes without the use of complicated and expensive instrumentation. In these instances, the one or more assay reagents can be selected so as to provide a response that is visible to the naked eye. For example, the assay reagent can be an indicator that exhibits colorimetric and/or fluorometric response in the presence of the analyte of interest. Indicators can include molecules that become colored in the presence of the analyte, change color in the presence of the analyte, or emit fluorescence, phosphorescence, or luminescence in the presence of the analyte. In some embodiments, the one or more assay reagents are selected to facilitate radiological, magnetic, optical, and/or electrical measurements used to identify and/or quantify one or more analytes in a liquid sample.

Depending on the analyte of interest, a wide variety of assay reagents can be incorporated into the assay regions. Examples of suitable assay reagents include antibodies, nucleic acids, aptamers, molecularly-imprinted polymers, molecular beacons, chemical receptors, proteins, peptides, inorganic compounds, nanoparticles, microparticles, and organic small molecules. The assay reagents can be applied to the microfluidic device by a variety of suitable methods. For example, one or more assay reagents can be deposited and/or immobilized within an assay region by applying a solution containing the one or more assay reagents, and allowing the solvent to evaporate.

In some instances, one or more assay reagents are non-covalently immobilized by physical absorption in or on the sensor or electrode assembly. The one or more assay reagents can be covalently linked to the substrate. Assay-reagents can be covalently immobilized using a variety of chemical techniques known in the art, including similar chemistry to that used to immobilize molecules on beads or glass slides, or to link molecules to carbohydrates. In particular embodiments, one or more assay reagents are covalently coupled to a cellulosic substrate via an ester, amide, inline, ether, carbon-carbon, carbon-nitrogen, carbon-oxygen, or oxygen-nitrogen bond.

The microfluidic device can include a suitable cover that seals or protects the top of the microfluidic channel. The cover can be formed from paper, glass, polymer, fabric, metal, and combinations thereof, with the provision that the material does not wet with the liquid flowing through the channel. Generally, the cover is a thin film or sheet, such as a polymer thin film. The cover can include a suitable opening to hold or secure the hydrogel in place when in use.

The microfluidic device can include one or a plurality of microneedles on the lower surface of the substrate, e.g. to penetrate the skin surface of the subject for continuous sampling of boduly fluids. Microneedles can include a variety of materials, including metals, ceramics, semiconductors, organics, polymers, and composites. For example, materials can include stainless steel, gold, titanium, nickel, iron, gold, tin, chromium, copper, alloys of these or other metals, silicon, silicon dioxide, and polymers. Generally, the microneedles should have the mechanical strength to remain intact and to serve as a conduit for the collection of biological fluid, such as interstitial or extracellular fluid, while being inserted into the skin, while remaining in place for up to a number of days, and while being removed.

Examples of suitable covers include, for example, thin films or sheets of polyethylene, polypropylene, such as high density polypropylene, polytetrafluoroethylene (PTFE), e.g., TEFLON™", polymethylmethacrylate, polycarbonate, polyethylene terephthalate, polystyrene or styrene copolymers, polyurethanes, polyesters, polycarbonates, polyureas, polyamides, polyethyleneamines, polyarylene sulfides, polysiloxanes, polydimethylsiloxanes, polyimides, polyacetates, and polyether ether ketone (PEEK).

The cover can be an adhesive sheet or tape that is adhered to the upper surface of the substrate. Any suitable adhesive tape can be used. Examples of suitable adhesive tapes include Scotch Tape 600, Scotch Tape 610, Scotch Tape 810, and Scotch Tape 811 (available from 3M, Minneapolis MN).

In some aspects, the lower surface of the substrate can include an adhesive or other material designed to temporarily adhere the device to a surface, e.g. the skin of a subject. In some aspects, the adhesive is a biologically safe adhesive. In some aspects, instead of or in addition to the adhesive, the device can include a strap configured to attach the device to a surface and to secure the device. For example. a strap can be configured to attach around an arm, leg, or other appendage of a subject in hold the device in place on the subject during use.

Methods of Making Microfluidic Devices

The appropriate methods for fabrication of the microfluidic devices can be selected in view of the type of microfluidic features present in the device, as well as the overall device design. Generally, fabrication of the microfluidic devices includes formation of a network of microfluidic components or equivalent paper conduits, application of the hydrogel, and application of a cover (when present). Fabrication may further include covalent modification of a substrate to modify the surface properties, e.g. to increase its hydrophobicity or increase the hydrophilicity of the paper strips. Such methods are known in the literature. Surface modification can include before, after, or both before and after the formation of the microfluidic components in the substrate.

Microfluidic devices can be fabricated into appropriate two- or three-dimensional shapes using a variety of methods. The substrates and/or covers can be mechanically cut, for example, by using a scissor, laser cutter, blade, knife, dye, or punch, to form a microfluidic device having the desired overall shape. In certain embodiments, the substrate and/or covers can also be perforated to facilitate folding or separation of the microfluidic devices after fabrication.

If desired, the shape of the device (and device components) can be designed on a computer using a layout editor or standard computer aided drafting software. The computer can be integrated with a laser cutter to automatically pattern the microfluidic device, and components thereof, into their desired shapes.

Microfluidic devices with paper conduits can be mass produced by incorporating highly developed technologies for automatic paper cutting, folding, embossing, etching, stacking, and screen-printing. In particular embodiments, the microfluidic devices are fabricated in series on a roll (e.g., roll-to-roll or reel-to-reel printing), or in the form of a single sheet containing multiple devices. In these embodiments, the substrate may be perforated to facilitate separation of one or more microfluidic devices from the roll or sheet. Adhesives can be applied to the devices using methods known in the art, for example, by rotogravure printing, knife coating, powder application, or spray coating. Suitable methods of application can be selected based on the surface(s) to the coated as well as the nature of the adhesive being applied. Adhesive can be applied to the devices, in a manner similar to labels, to permit the devices to be adhered to a surface.

Microfluidic channels, collection pads, evaporative pumps, and other features can be fabricated by embossing, stamping, or impressing a substrate. Channels can be embossed using a pair of dies (i.e., positive and negative) having complementary shape and appropriate design for the desired channel. A sheet of substrate can then be placed between the pair of dies, and pressure is applied to emboss the substrate, forming an open channel within the substrate. Suitable dies can be fabricated from a variety of materials, including metals, polymers, and combinations thereof.

Typically, the porous, hydrophilic substrate is first patterned to form the shape of the channels, collection pads, evaporative pumps, and other features. The porous hydrophilic substrates, paper strips, evaporation pads, and the like may be mechanically cut, for example, by using a scissor, laser cutter, blade, knife, dye, or punch, and embedded to form a microfluidic device having the desired overall shape. A cover can subsequently be applied over all or a part of the porous, hydrophilic substrate and so as to seal the closed channel.

Microneedles can be constructed from a variety of materials, including metals, ceramics, semiconductors, organics, polymers, and composites. For example, materials of construction can include stainless steel, gold, titanium, nickel, iron, gold, tin, chromium, copper, alloys of these or other metals, silicon, silicon dioxide, and polymers. Generally, the microneedles should have the mechanical strength to remain intact and to serve as a conduit for the collection of biological fluid, while being inserted into the skin, while remaining in place for up to a number of days, and while being removed.

Figure 9A:
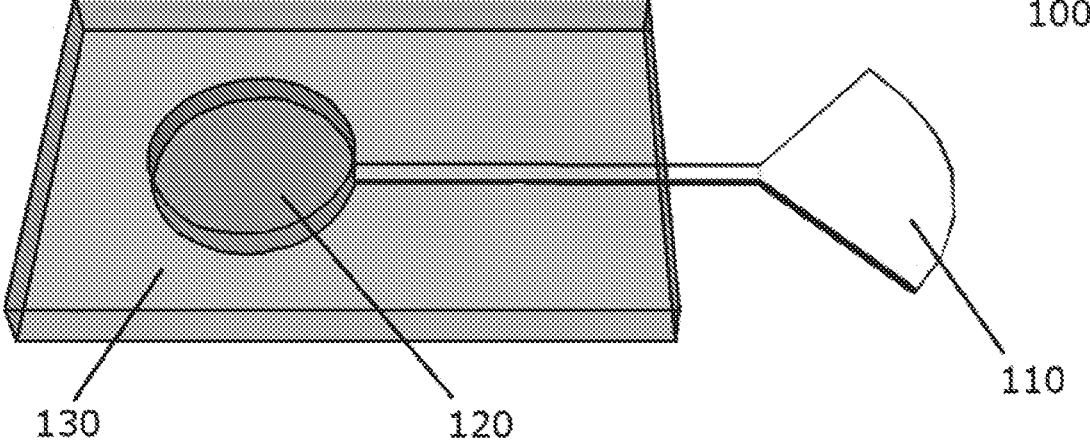
FIGS. 9A-9C depict an exemplary microfluidic device for continual sampling of interstitial fluid and sweat.
Figure 9B:
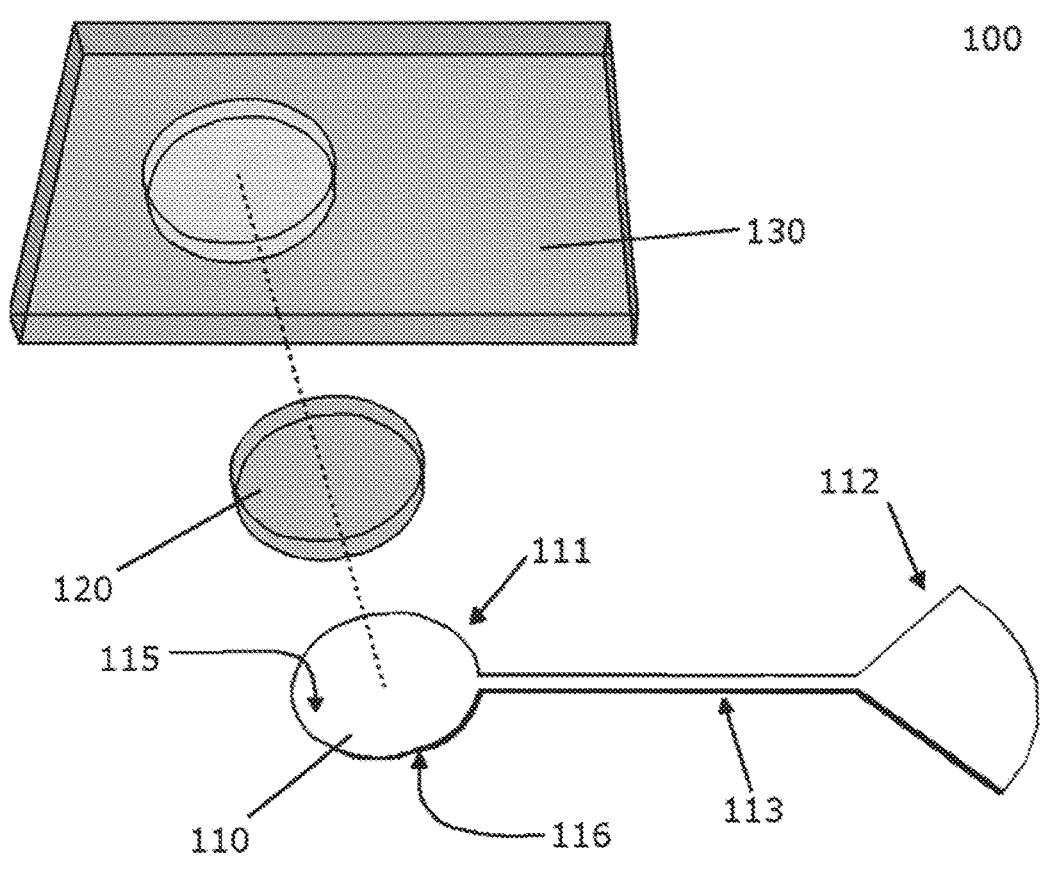
Figure 9C:
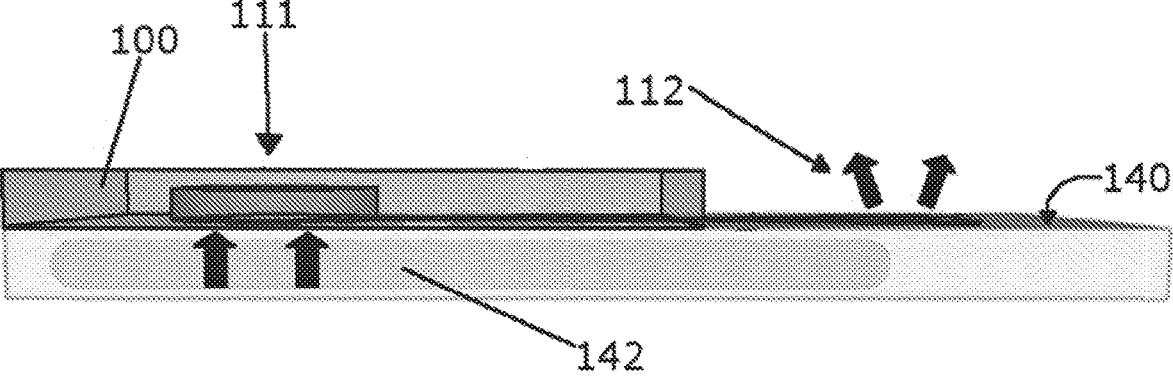
Figure 9D:
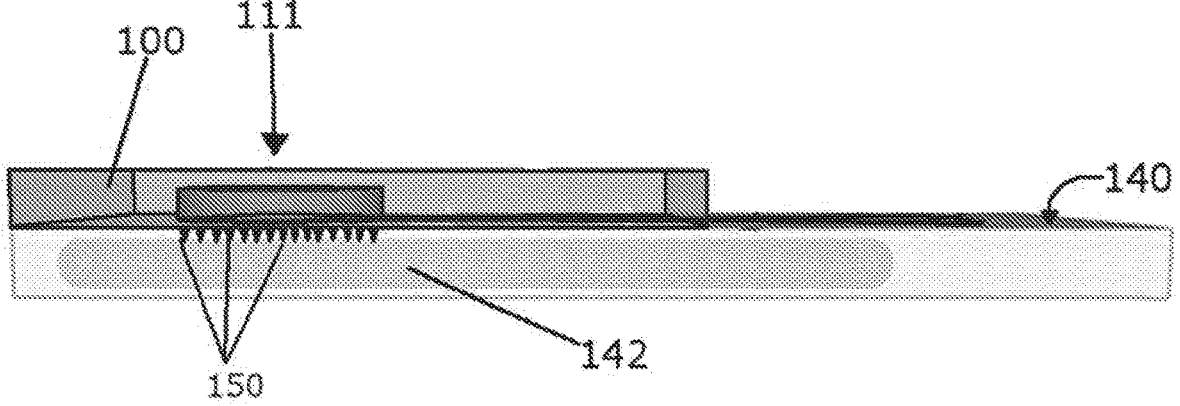
FIG. 9D is a side view of an alternative exemplary microfluidic device having a plurality of microneedles for penetrating the skin of the subject.
Figure 10A:
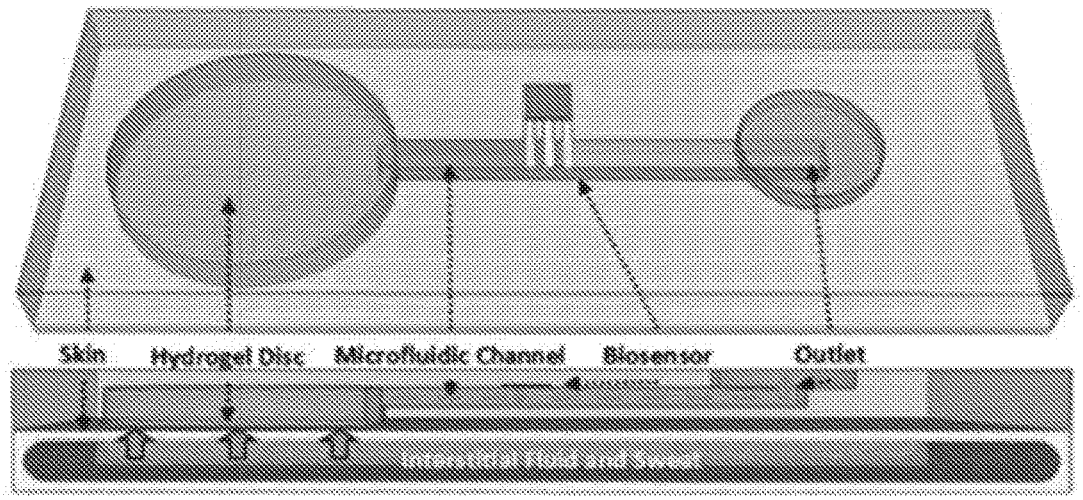
FIGS. 10A-10F demonstrate results for an exemplary embodiment of a hydrogel based microfluidic pumping platform.
Figure 10B:
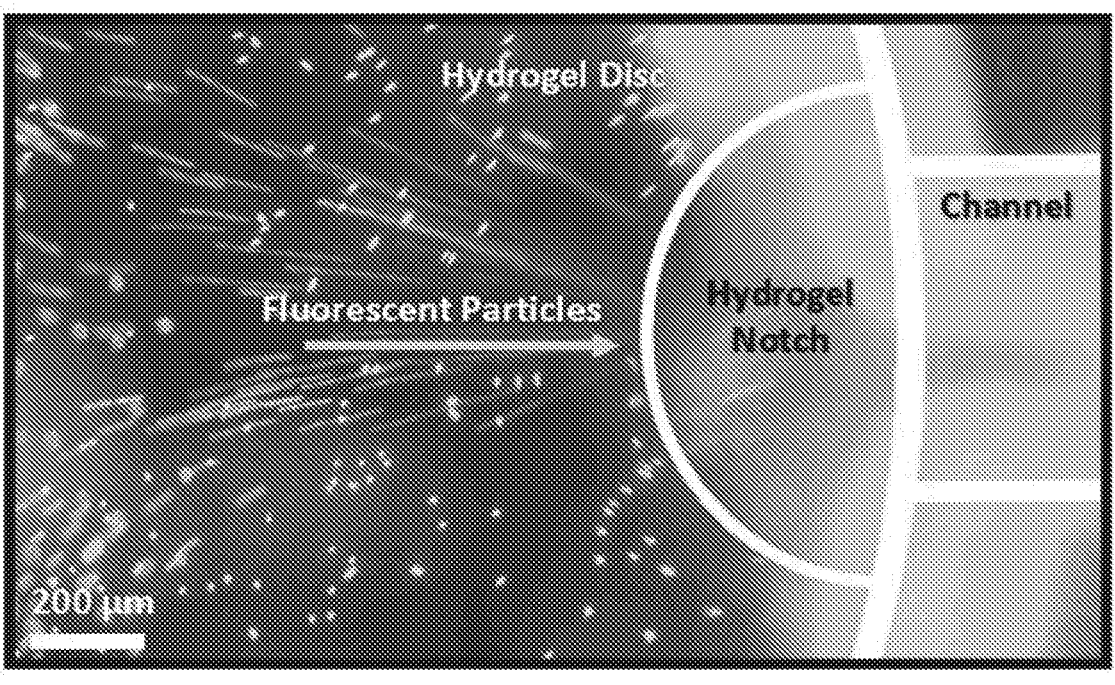
Figure 10C:
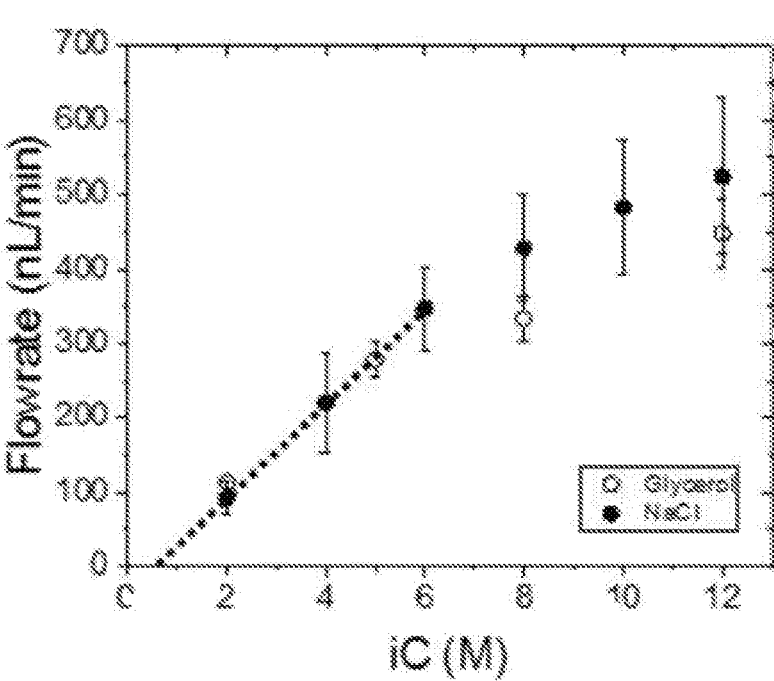
Figure 10D:
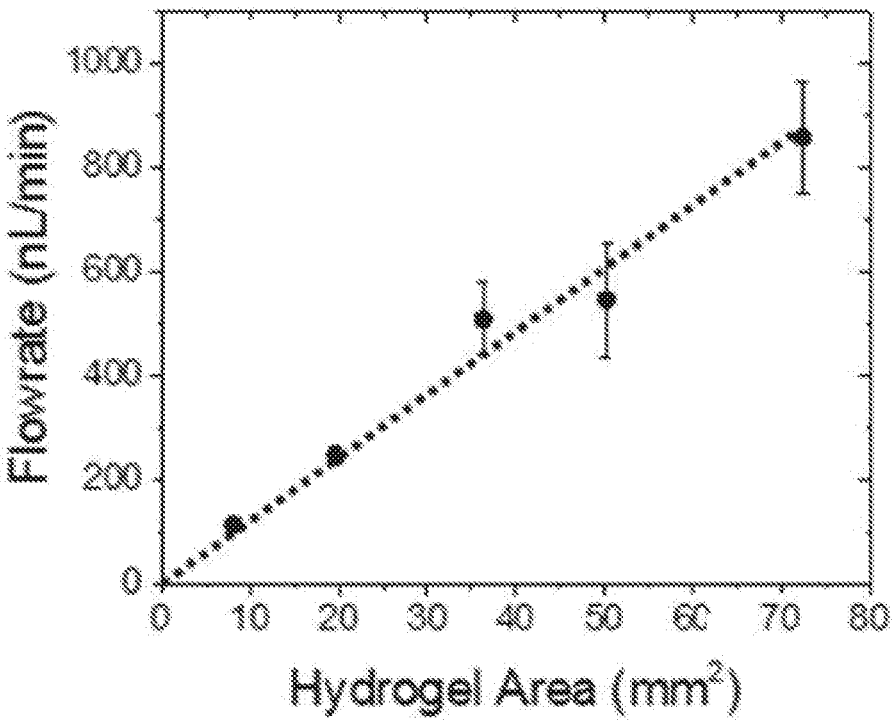
Figure 10E:
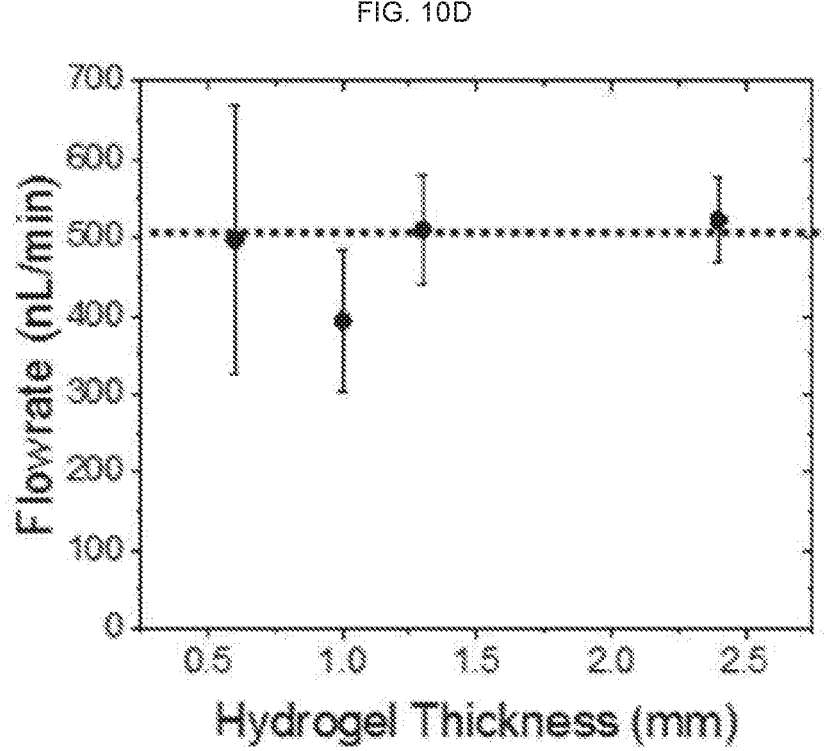
Figure 10F:
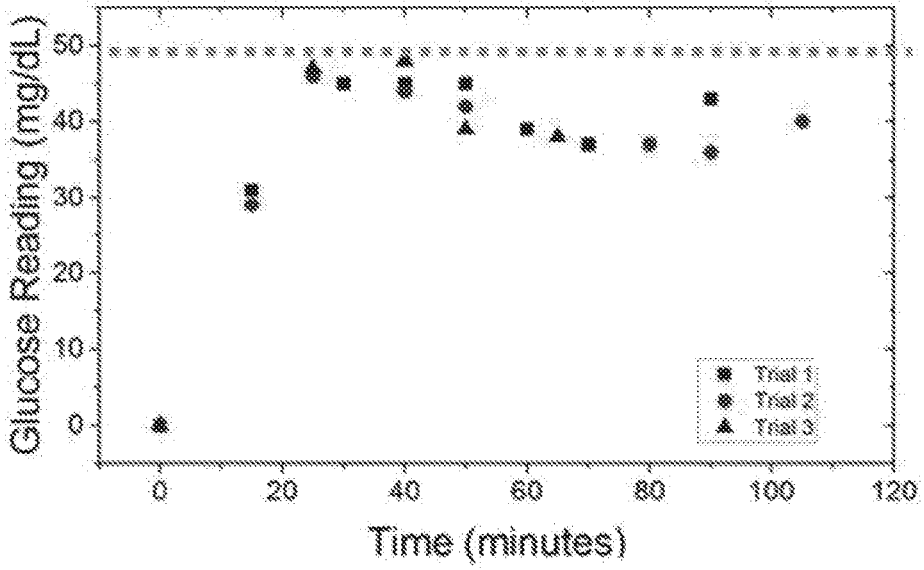

An exemplary microfluidic device 100 for continual sampling of sweat or other bodily fluids is depicted in FIGS. 9A-9C. The device 100 a structure 130 that includes a porous hydrophilic substrate 110 containing a collection pad 111 for collecting sweat, interstitial, or other bodily fluid; a semicircular evaporation pad 112 that acts as an evaporative pump, and a channel 113 connecting the collection pad 111 and the evaporation pad 112. The substrate 110 has both an upper surface 115 and a lower surface 116. The device 100 includes a hydrogel 120 on the upper surface 115 of the substrate 110 in the region of the collection pad 111, the hydrogel including a plurality of extractants (not pictured) to drive the flow of the fluid 142 into the collection pad 111 when in use. The device 100 can be placed on the skin surface 140 of a subject, with the lower surface 116 contacting the skin surface 140 to provide sampling of a bodily fluid 142 from below the skin surface 140 by continually drawing the fluid 142 into the substrate 110 in the region of the collection pad 111 and through the channel 113 to the evaporation pad 112. In an alternative aspect, as depicted in FIG. 9D, the device 100 can include one or a plurality of microneedles 150 attached or adhered to the lower surface 116 for penetrating the skin surface 140.

Methods of Using Microfluidic Devices

Methods of using the microfluidic devices are also provided, for example for the detection of an analyte in a fluid. Suitable fluids can include water, blood, urine, saliva, sweat, tissue exudate, tissue transudate, or a combination thereof. The methods can include placing the lower surface of a microfluidic device above the fluid (for example, on the skin of a subject such as a human), and measuring the analyte in the fluid by detecting the analyte with a sensor as it passes through the channel in the microfluidic device. The methods can include placing the lower surface of a microfluidic device above the fluid, and measuring the analyte in the fluid by detecting a colorimetric and/or fluorometric response to the presence of the analyte.

The step of placing the lower surface above the fluid can include placing the microfluidic device on a skin of a subject. The devices are particularly suited for applications for monitoring the presence of an analyte in sweat. The sweat can be from any subject, including any mammalian subject such as humans or a suitable veterinary animal. The methods can include detecting analytes in other fluids such as water, blood, urine, saliva, tissue exudate, tissue transudate, and a combination thereof. Because the hydrogel has a higher osmotic pressure than the fluid, the fluid is pumped into the collection pad of the substrate. The extractants in the hydrogel create an osmotic driving force pulling the fluid into the collection pad of the microfluidic device.

The methods can be used to analyze a variety of analytes. In some aspects, the analyte is selected from the group consisting of glucose, uric acid, lactic acid, cortisol, nitrates, and cholesterol. The fluid can be continually monitored for a period of time from about 5 hours to about 10 days, about 10 hours to about 10 days or about 1 day to about 10 days. The fluid can be continually pumped with a linear flow rate of about 0.1 mm/min to 10 mm/min.

The analyte can be measured using any of a variety of biochemical sensors along the channel. In some aspects, the device has an evaporation pad, and the method includes measuring the amount of analyte on the evaporation pad after the device has been used for a period of time. For example, the total levels of the analyte in the subject can be correlated to the total amount of the analyte on the evaporation pad after the period of time. Likewise, because the analyte is deposited on the evaporation pad at different locations at each period of time, the concentration of the analyte of a given point in time can be determined by measuring the concentration levels at points in the evaporation pad.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1. Sample Device Fabrication and Experimental Setup

Materials

The hydrogels were created using acrylamide as the monomer, n,n'-methylenebisacrylamide as the crosslinker and 2-hydroxy-4'-(2-hydroxyethoxy)-2-methylpropiophenone as the photoinitiator (all from Sigma). PDMS devices are created using Sylgard 184 (Dow Corning). Microfluidic molds were created using SU8-100 photoresist (Microchem) on silicon wafers. Solid sodium chloride (Sigma) was used to prepare sweat solutions while tablets are used to create phosphate buffer solutions (PBS) solutions.

Device and Hydrogel Fabrication

The PDMS microfluidic devices were created using traditional techniques. First, molds were created using SU8-100 photoresist on silicon wafers by means of lithography. A 10:1 mixture of Sylgard 184 was prepared and degassed using a Thinky mixer AR-1000. PDMS was then cured on a mold and on a flat surface in a 70° C. oven for 1 hour. Metal leather punch dyes were used to cut the holes in PDMS. Oxygen plasma treatment was then performed to bind the pieces together to create the microfluidic devices.

Polymerization of the hydrogel was performed under a 100 mW UV lamp for 1 minute. After polymerization was complete, the hydrogels were allowed to equilibrate in solutions of sodium chloride for at least 24 hours. Hydrogel discs were cut from swollen sheets of hydrogels using a laser cutter. Designs were created in CorelDraw and cut using a laser cutter. A power level of 100% and speed of 15% was used. Multiple cuts were performed three times in a row to ensure the hydrogel had been fully cut through. These hydrogels were then placed back into their NaCl solution until testing was to be performed.

Experimental Procedure

We sought to show that the hydrogels were capable of pulling water through a membrane as a proof of principle to show it was possible to do the same against skin. Methods and schematics for the experimental setup can be seen in FIGS. 1A-1D. The previously cut hydrogel discs were removed from solution and blotted with a Kimwipe to remove excess water from the surface. The hydrogel disc was then placed in the opening on the PDMS device and a razor blade was then used to cut off any hydrogel extending past the surface of the PDMS as to create a smooth surface. Dialysis tubing was cut and placed on the bottom side of the hydrogel disc to act as a skin-like membrane. The PDMS device was then clamped in place on the diffusion cell and the chamber is filled with a phosphate buffer solution which was meant to mimic an isotonic solution of sweat in the body.

A compact diffusion cell was designed to be placed onto the stage of a microscope to allow the flow through the channels to be observed visually. During early stages of fluid intake, the front of fluid traveling through the microchannel was tracked to determine a flow rate. Flow was observed using 5 μm magnetic fluorescent tracer particles once the fluid had filled the entire channel and there was no longer a fluid front to follow. Using fluorescence microscopy, particle velocity was then calculated in the microchannel and correlated to flow rate.

Results and Discussion

Osmotic Driving Force and Notched Hydrogel Design

Hydrogels were infused with solutions of both fixed and free ions. Fixed ions were chemically bound to the backbone of the polymer and were not free to move. Free ions were ionic species that were dissolved in the water contained in the hydrogel matrix and could move freely. Both fixed and free ions in the hydrogel created osmotic pressure differences with the solution below the membrane. Fluid flow through the membrane as driven by this osmotic pressure difference between the hydrogel and the solution beneath the membrane was approximated using the equation below. Osmotic pressure (Π) is directly related to the Van't Hoff factor (i), gas constant (R), temperature (T) and the respected concentration difference between the hydrogel and the sweat.

$$\Pi=iRT\Delta C=iRT(C_{Gel}-C_{Sweat})$$

Figure 1A:
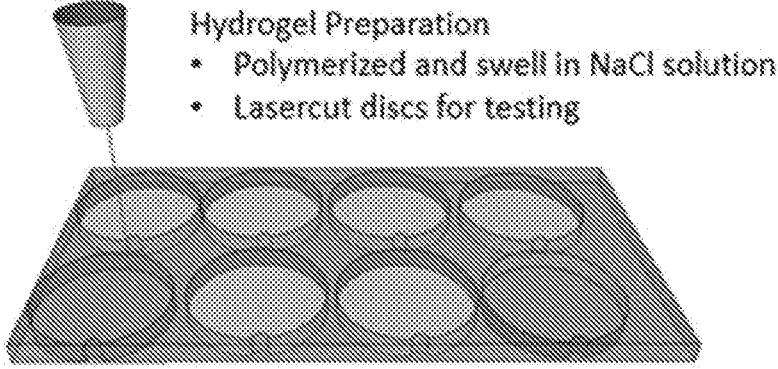
FIGS. 1A-1D depict a schematic of how the hydrogel discs are created (FIG. 1A), PDMS microfluidic devices are fabricated (FIG. 1B), testing is set up (FIG. 1C) and an image of what the device looks like under the microscope (FIG. 1D).
Figure 1B:
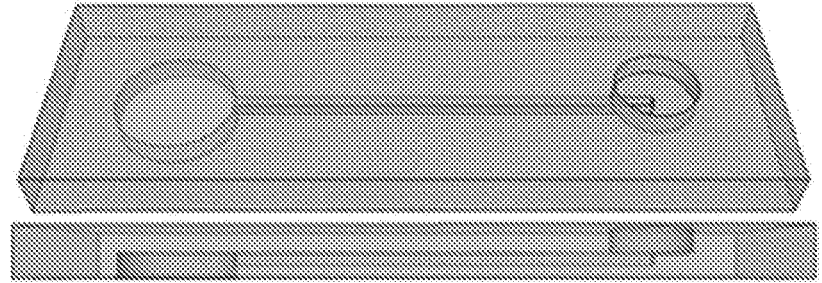
Figure 1C:
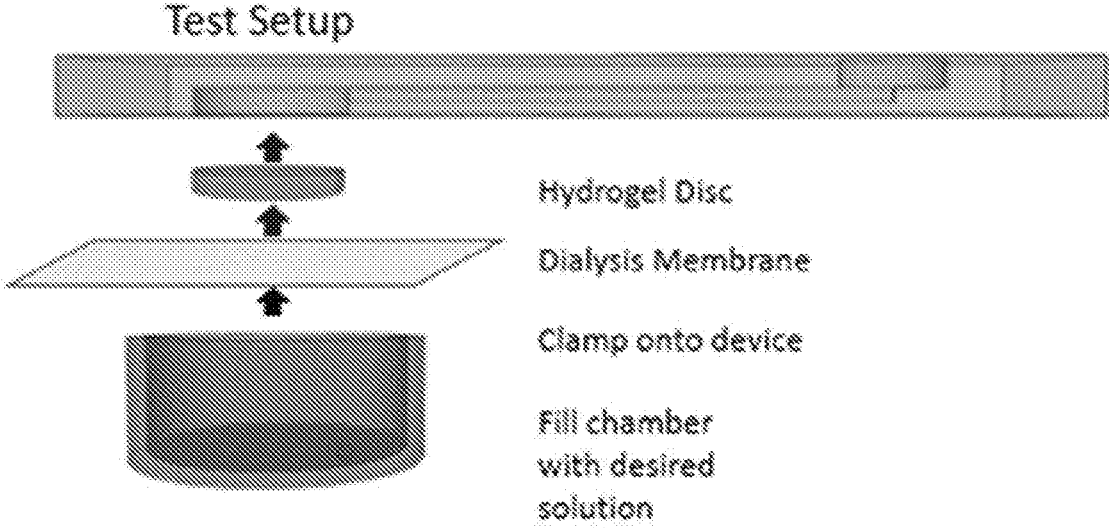
Figure 1D:
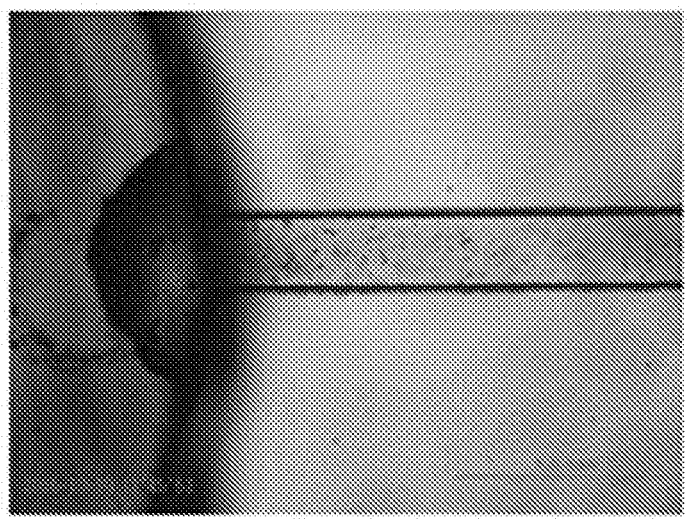
Figures 2A, 2B:
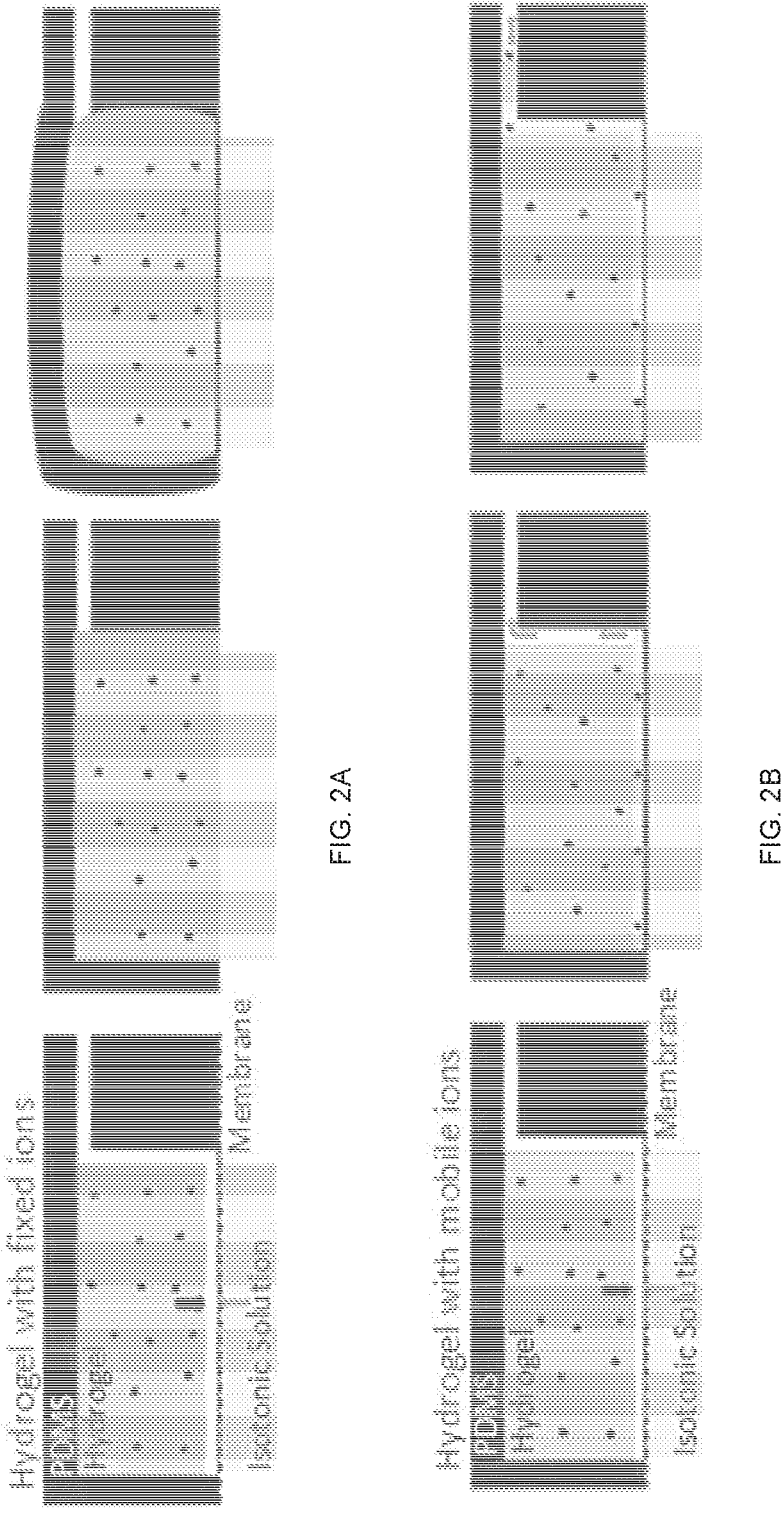
FIGS. 2A-2B depict a schematic showing mechanism of fluid flow from the isotonic solution in the lower chamber through the microchannel. The mechanisms driving fluid flow for both hydrogels with fixed (FIG. 2A) and mobile (FIG. 2B) ions are shown.

Chemical species were selected to create a high osmotic pressure difference between the hydrogel and the body (here, mimicked by a salt solution across a membrane). Although both fixed and free ions create this pressure difference with the isotonic solution, the free ions allowed for flow into the attached microfluidic channel. Fixed ions created a high pressure difference with the solution but only served to drive fluid flow into the hydrogel. This resulted in a swelling of the hydrogel but not in pumping of fluid in the microchannel. In order to obtain this push and pull mechanism with the fluid, hydrogels with high mobile ion concentrations were required. Mobile ions still created the same osmotic pressure difference with the solution which pulls the fluid through the membrane. The difference here was that salt ions could then diffuse out of the hydrogel and mix with this fluid as it is passed through the channels or equivalent paper conduits. This mixing of salt allows for a uniform ionic strength between the hydrogel and fluid in the microchannel, so as to not create an osmotic back pressure. A schematic can be seen in FIGS. 2A-2B.

Figure 3:
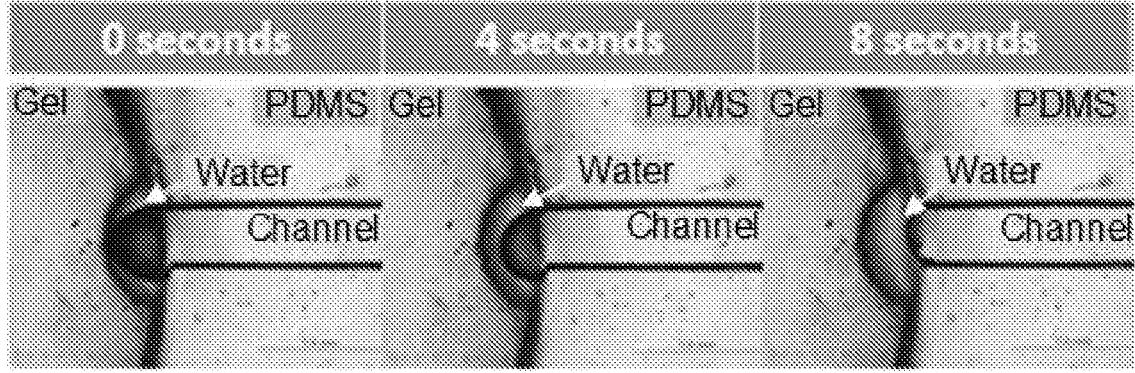
FIG. 3 depicts a series of microscope images over time showing how fluid drawn initially through the membrane is drawn to this void area created by the notch in the hydrogel. The fluid first fills this void and then enters the microchannel, expelling the air in the system first.
Figure 3:
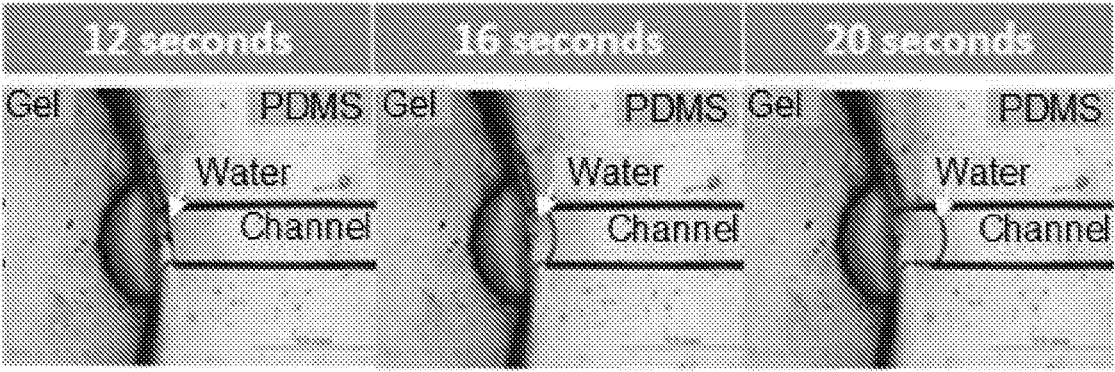

One important feature of the device was how the hydrogel disc fit in the 'well' in the PDMS. Fluid started passing through the membrane as soon as it came in contact with the hydrogel. As the fluid passed through the membrane, a thin fluidic layer formed between the hydrogel and the membrane. It is in this layer that salt was transferred from the hydrogel to mix with this fluid due to the ionic pressure difference. Fluid was continually pumped through the membrane and is eventually driven towards the microfluidic channel in contact with the hydrogel. In this regime, the flow is governed by the path of lowest hydrodynamic force. Small semi-circle notches (radius of 0.375 mm) were cut into the sides of these hydrogels to help reduce resistance. These void spots created a low pressure area to accept and thus guide the fluid flow. Fluid drawn through the membrane proceeded to this area as it had a lower resistance due to the open space. As fluid collected in this area, any remaining air bubbles were passed through the microchannel until the fluid reaches the channel opening. At this time the fluid was driven directly into the channel. This predesigned path for the fluid allowed for a guided and controlled flow with more consistent flow rates. FIG. 3 demonstrates this property of the notched hydrogel.

Hydrogel Effects on Flow Rate: Molarity and Geometry

Figure 4A:
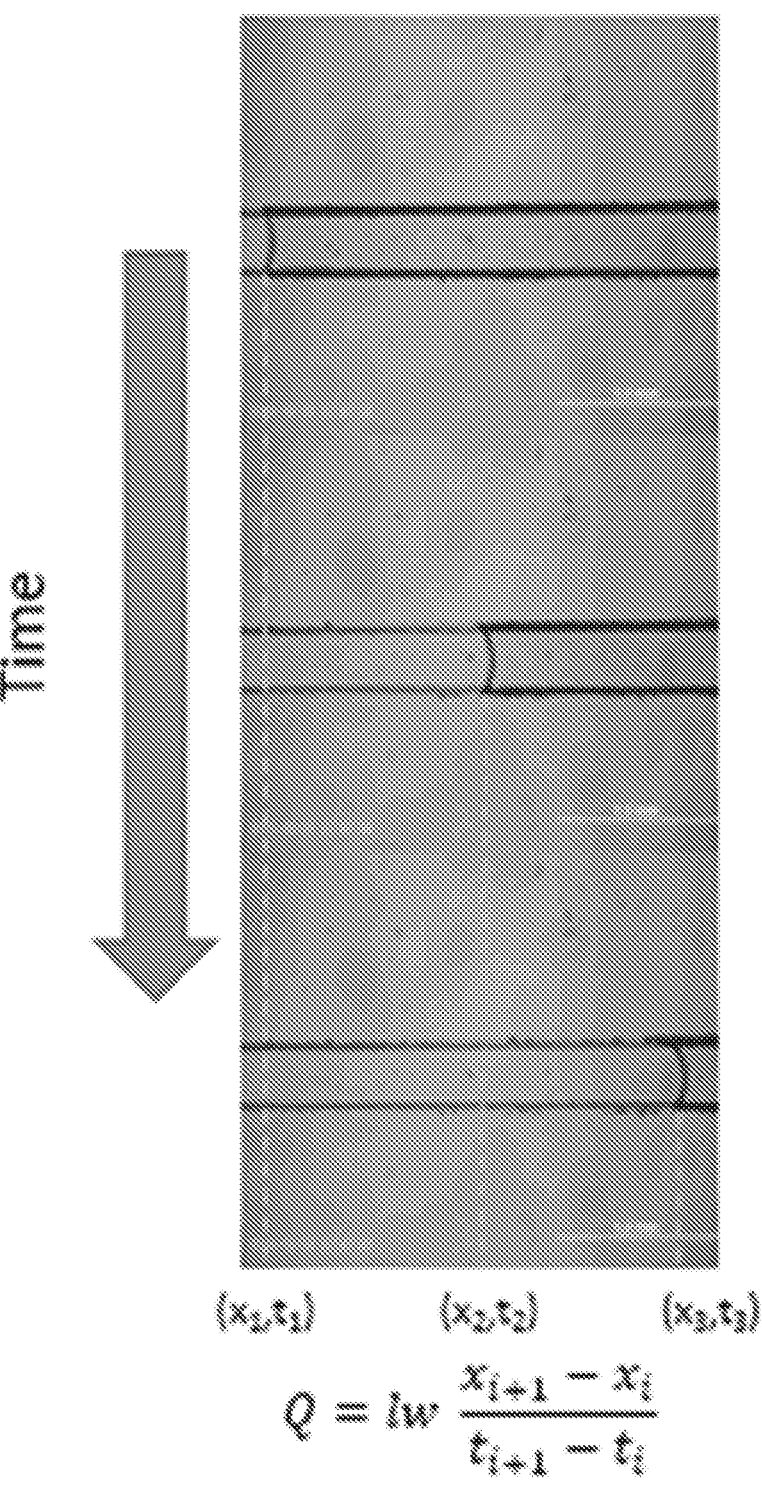
FIGS. 4A-4B depict how flow rate is calculated (FIG. 4A) and flowrate plotted vs sodium chloride concentration (FIG. 4B).
Figure 4B:
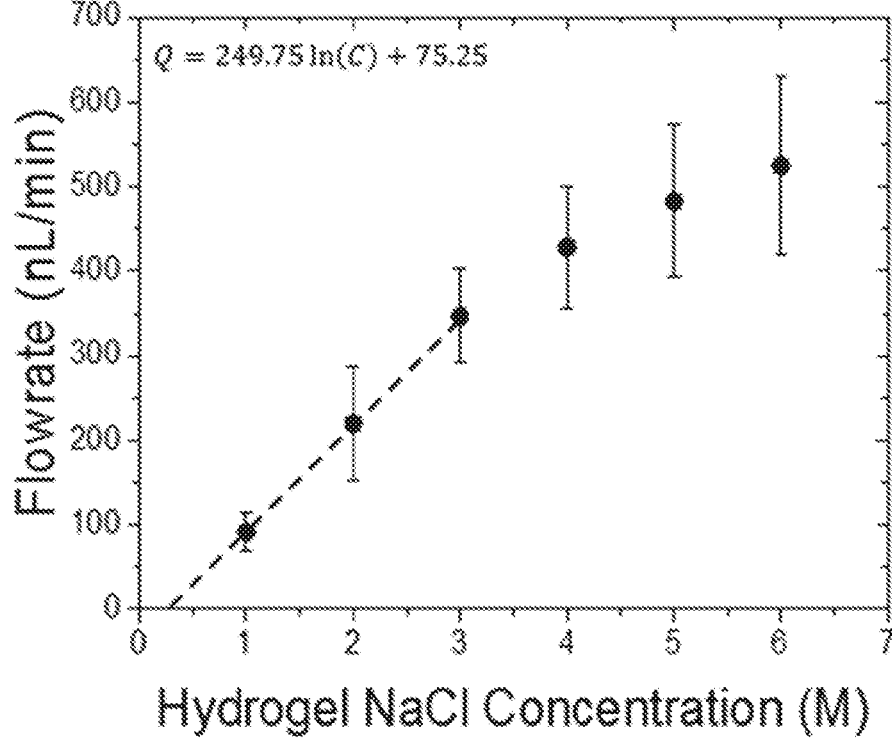

Hydrogels with ionic strength ranging from 1 to 6M NaCl were tested while flow rate through the microfluidic device was monitored. The velocity of the fluid front was measured over time to obtain a flowrate. These flow rates and their correlation to ionic strength can be seen in FIGS. 4A-4B.

Increased salt concentrations resulted in an increased flowrate through the microchannel. Between concentrations of one and three molar a linear trend can be observed. By regressing this line, an x intercept of 0.28 M is calculated. The concentration between the hydrogel and the body must be greater than zero for any flow to occur. The isotonic solution used has an ionic strength of roughly 0.15 M. Therefore, this x intercept slightly above that of the isotonic concentration agrees with theory.

Figure 5A:
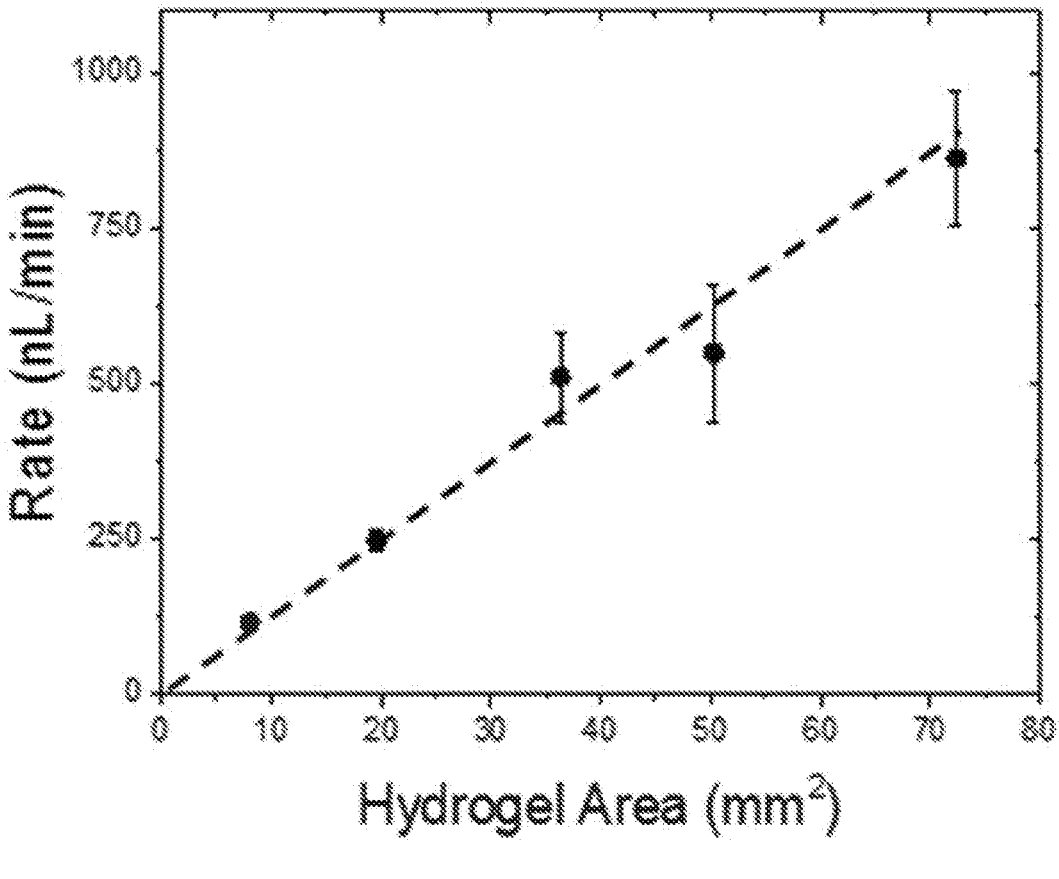
FIGS. 5A-5B are graphs showing the effect of the hydrogels surface area (FIG. 5A) and thickness (FIG. 5B) on flowrates obtained.
Figure 5B:
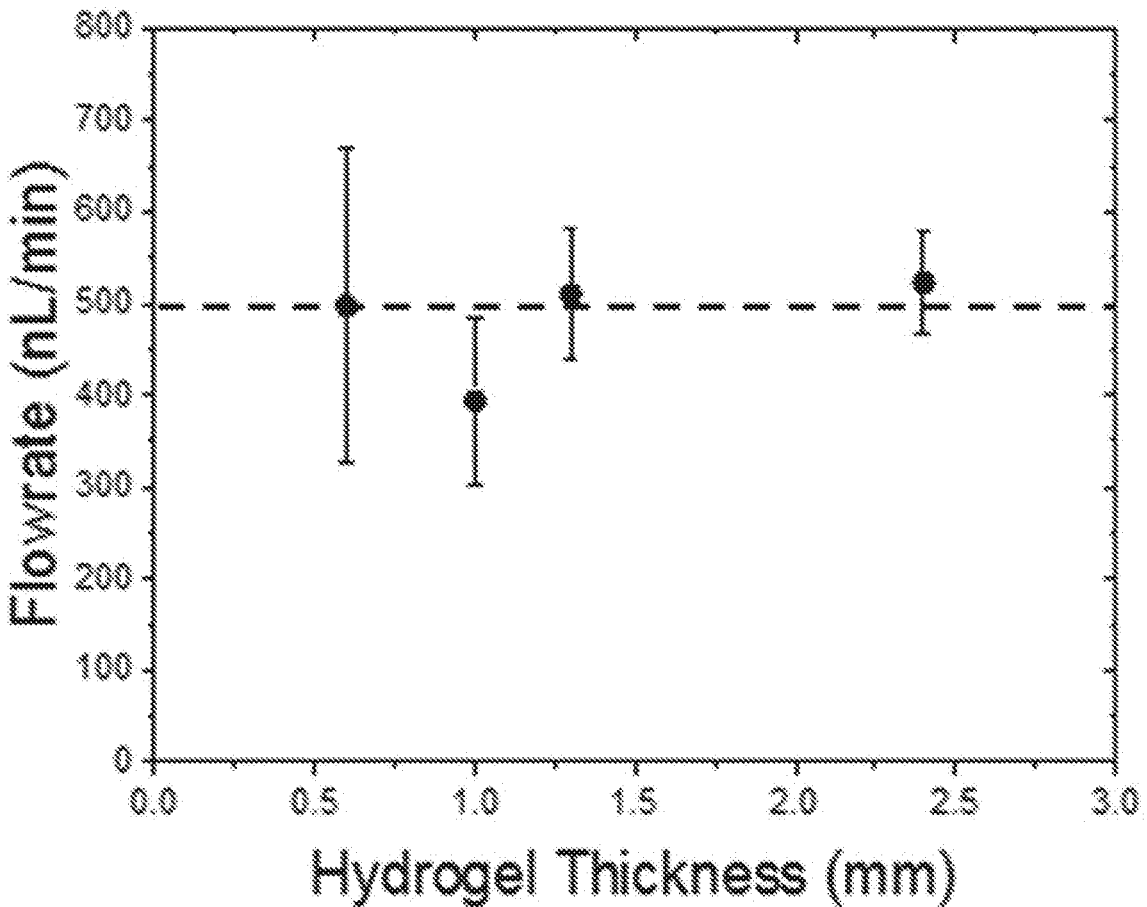

Tests were performed using hydrogels with varying diameters and thicknesses to determine how geometry affects the flowrate. Flowrate theoretically should be directly related to surface area as an osmotic pressure across a membrane creates a fluid flux (flow per unit area). Therefore, as the surface are increases there should be a linear increase in flowrate. The thickness of the hydrogel should not have an effect on flow rate as both the osmotic pressure of the hydrogel and surface area of contact remain the same. The results can be seen in FIGS. 5A-5B.

Long Duration Particle Tracking

Figures 6, 7A:
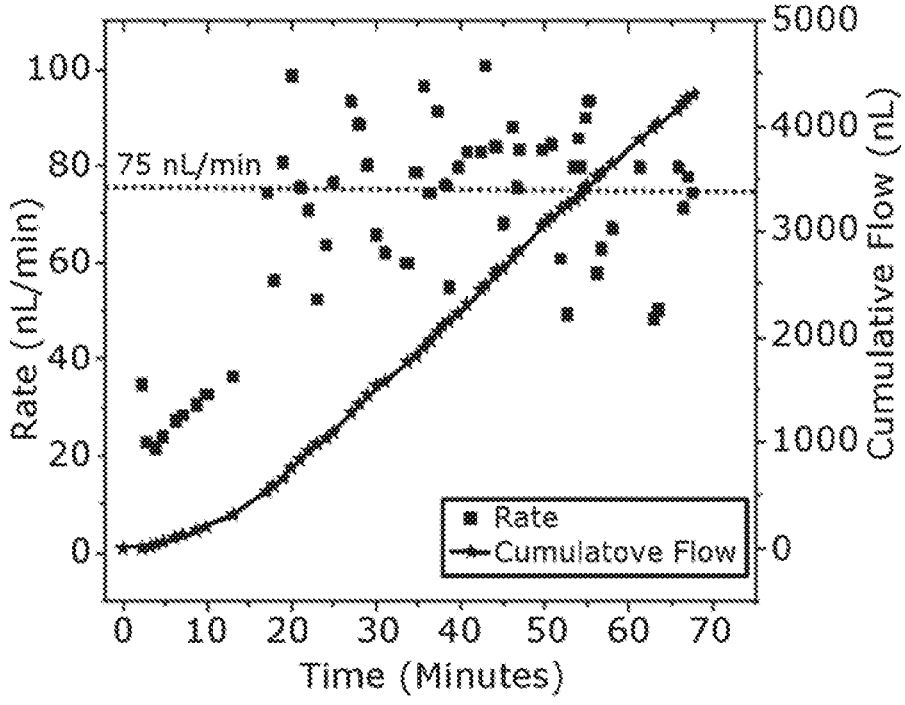
FIG. 6 shows a graph of flowrate over time measured using microfluidic fluorescent particle tracking.
FIGS. 7A-7C demonstrate one embodiment of how the fluid flowing through the channel of an exemplary microfluidic device can be correlated to the chamber.

Particle tracking was used with microfluidic devices to record long term flow rates for the PDMS devices. Photos were taken using a long exposure (0.2 seconds) for these tests. When moving particles are photographed using a long exposure, a streak is captured as the particles moves with the fluid. By measuring the length of this streak and dividing by the exposure time, the velocity of the particle can be inferred. These particles were deposited on the PDMS surface of the well where the hydrogel disc is placed prior to testing. Magnetic fields can be applied to briefly perturb these particles which causes them to be dragged into the streamlines of the fluid flow. Perturbed particles then get pulled by the convective fluid flow and travel through the microchannel where they can be tracked. FIG. 6 shows the tracked rate over time for a trial measured using microfluidic fluorescent particle tracking. This test showed flow for over one hour. The longest observed test has shown a measureable flow rate for over 2½ hours.

Determining the exact flow rate can be difficult as the correlation between particle velocity and flow rate will be highly dependent on location of the particle in cross-section of the channel. Laminar flow was observed which resulted in a parabolic flow profile with respect to the geometry. This test demonstrates that fluid is being continually pumped for durations of up two hours.

Fluorescent Fluid Tracking

Figure 7B:
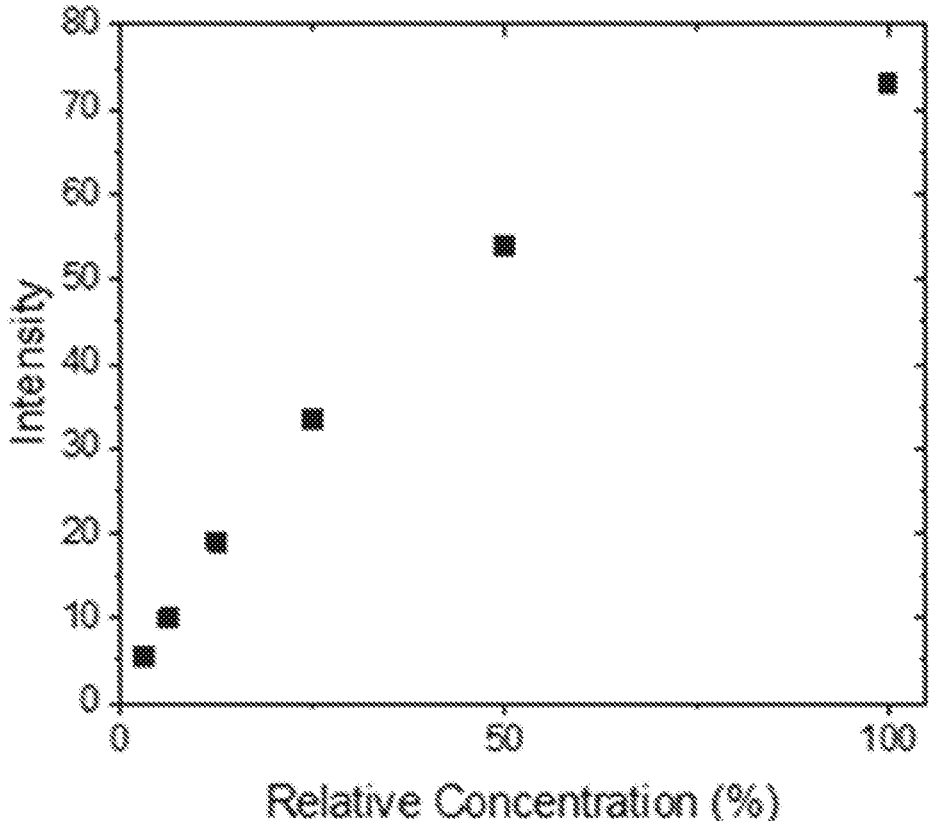
Figure 7C:
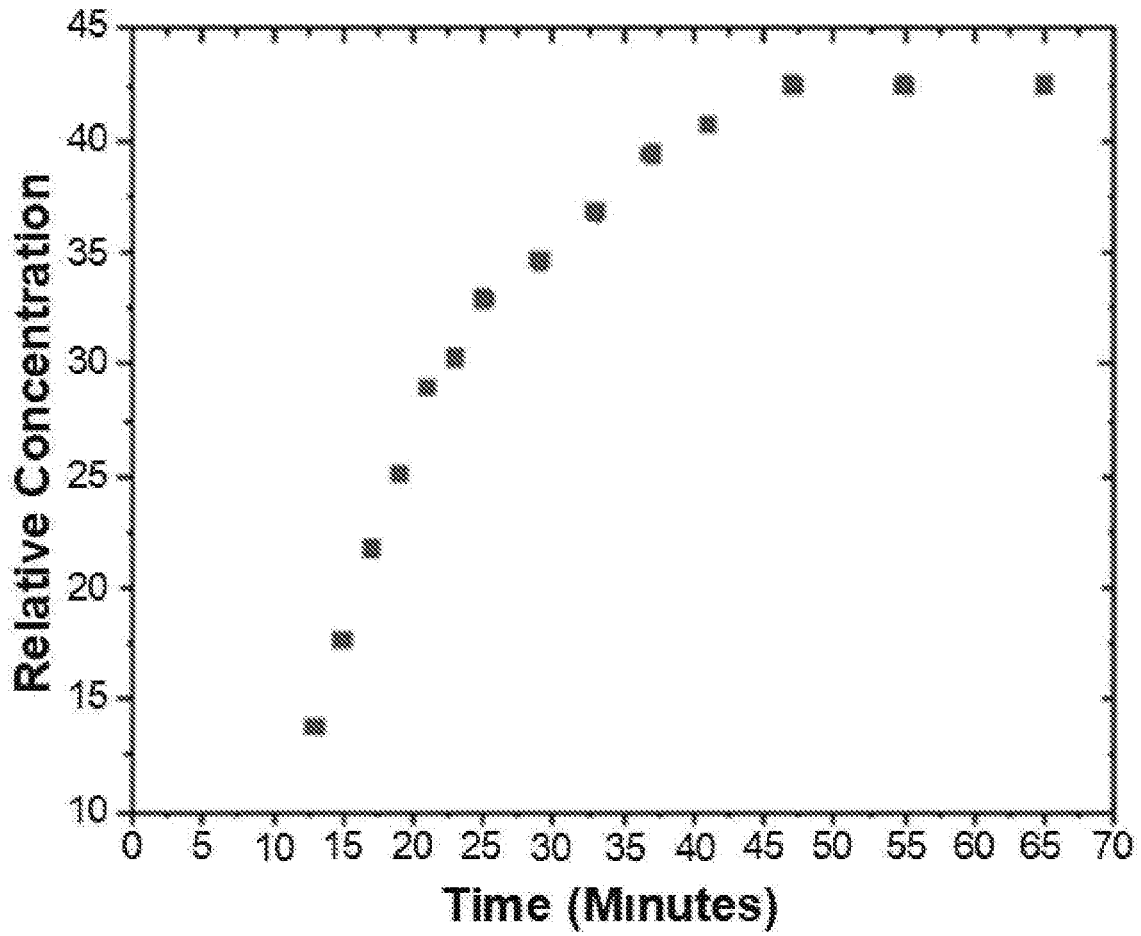

The ionic hydrogels have the capability of drawing in fluid and pumping it to a microfluidic channel for long durations. To be an effective pump for sensing purposes, the device needs to be able to pump both the fluid and the analytes in solution. To demonstrate this property, the chamber was filled with a PBS solution that had a fluorescent dye dissolved in it. We then observed the microfluidic channel under a fluorescent microscope. Initially, there was no fluorescent material in the channel and it appeared dark. As the fluorescent fluid was pumped from the chamber, it made its way through the membrane and into the channel. FIG. 7A shows the resulting images on the left side of the figure. A calibration (FIG. 7B) was created that correlated light intensity of the fluorescent channel to the concentration of the fluid in the chamber. Therefore a 0% concentration represented no fluorescent material while a 100% concentration meant the fluid in the channel has the same fluorescence of the fluid in the chamber. As can be seen in FIG. 7C, 13 minutes from the start of the test was when fluorescence was first observed in the channel. After 45 minutes, the concentration leveled out to roughly 43% of that in the chamber. This test demonstrates that our pumping mechanism was able to pump both solution and it's analytes into the microfluidic channel, where sensing can later take place.

Model

Flowrate measurements were obtained for hydrogel rates of varying geometry and ionic concentrations. Mathematical models were obtained from these correlations. A numerical model was created from analytic correlations that can be used to predict flow rate and hydrogel concentration over times.

testing. The acrylic is held vertically 2 cm above the lab table with the strips hanging below. A Canon EOS Mark5 DSLR camera was placed on the table ranging from 15-30 cm away and focused on the strip. Manual mode was used with an ISO of 400 and exposure of $\frac{1}{13}$ seconds. Six black (UV) LED lights, from an ACLOROL 5050 LED strip, were placed approximately 2 inches in front of the paper strips to illuminate the fluorescent dye. A cardboard enclosure surrounded the setup to block external light from affecting the images. The camera took photos every 30 seconds to obtain time-lapse images of the fluorescent dye moving through the paper. All tests were performed in ambient lab conditions ($\sim 70°$ F. and 40% RH). Fluctuations in these conditions may occur and can be a cause of error in measurements.

The strips are initially suspended with the sampling region interfacing DI water to allow for wicking to fully wet the strip. Once fully wetted, a solution of a fluorescent fluid is placed at the bottom of the strips. It is the motion of this dye that is tracked. Depending on the test performed, the sampled solution may be switched mid test between DI water and samples with varying dye concentration. For the long duration tests, the paper strips were kept in contact with PBS water continually over the ten day span. Fluorescent dye was introduced as stated above once a day in order to

| | Volume | Concentration | Flow Rate |
|---|---|---|---|
| Analytic | $V = V_0 + \int_0^t q\,dt$ | $C_{gel} = \dfrac{n_0}{V}$ | $Q = [249.8 \ln(C) + 75.25]\left(\dfrac{R}{R_{ref}}\right)^2$ |
| Numeric | $V_{i+1} = V_i + Q_i\Delta t$ | $C_{i+1} = \dfrac{n_0}{V_{i+1}}$ | $Q_{i+1} = [249.8 \ln(C_{i+1}) + 75.25]\left(\dfrac{R}{R_{ref}}\right)^2$ |

Figure 8A:
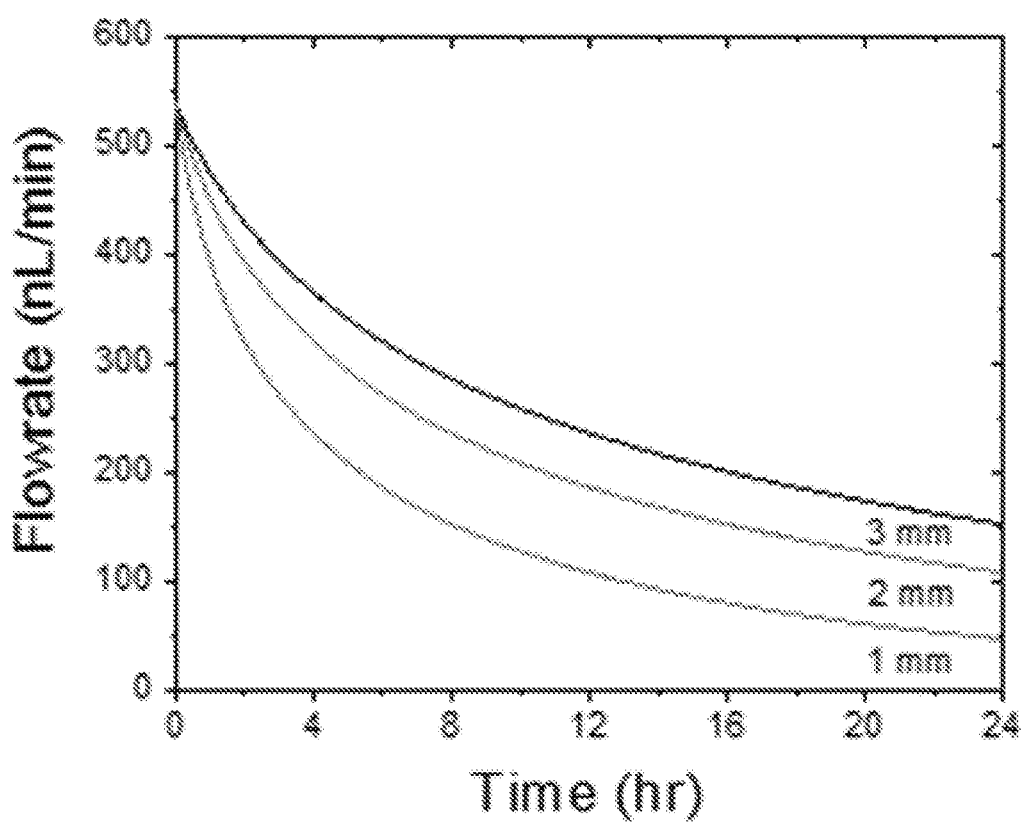
FIGS. 8A-8B demonstrate an example of a model evaluating how flowrate (FIG. 8A) and hydrogel concentration (FIG. 8B) decrease over a 24 hour span for hydrogels ranging in thickness from 1-3 mm.
Figure 8B:
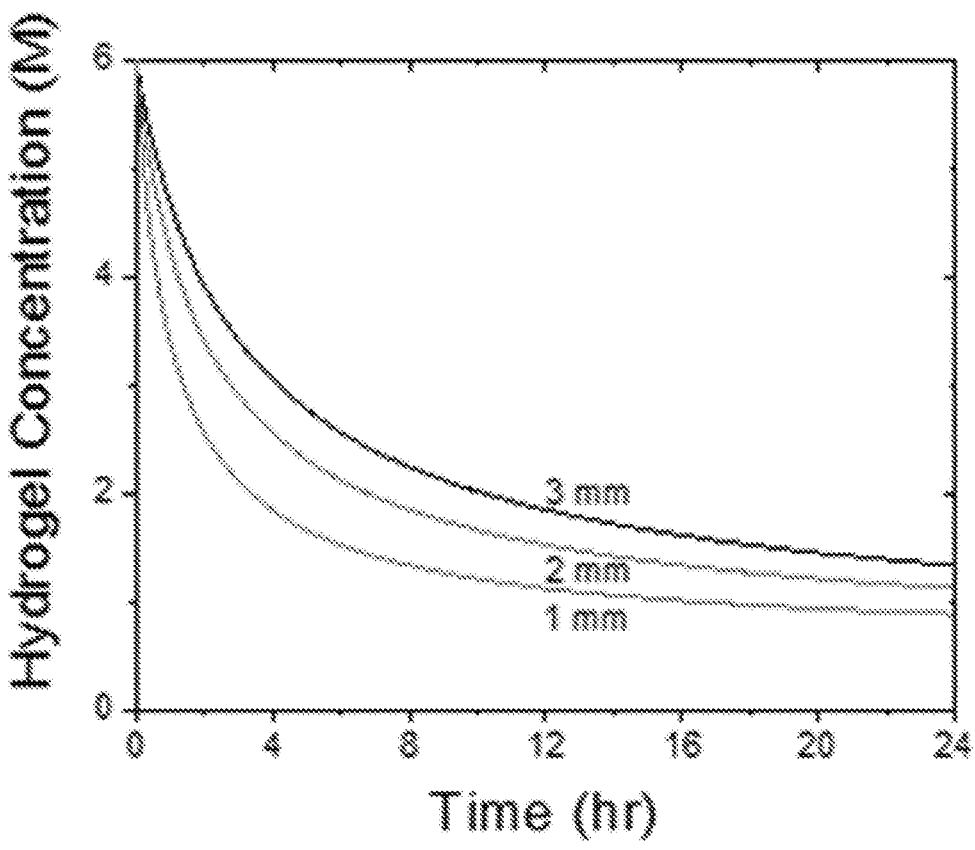

Using this model, the only parameters that needed to be entered were the initial geometry and concentration of the hydrogel, all of which are known. FIGS. 8A-8B show how the concentration and flowrate of hydrogels are expected to change over time for hydrogels of varying thickness. While hydrogel thickness was shown not to affect flow rate, it does create a larger hydrogel volume which dilutes slower over time. This slower dilution keeps concentration and flowrate up allowing for longer durations when testing.

Example 2. Long-Term Evaporative Pumping in Paper Microfluidic Device

Methods

Materials. Whatman quantitative filter papers, hardened, asheless, Grade 542 (GE Healthcare Life Sciences) were used. Our designs consist of three main features; a sampling interface where the paper is in contact with the desired fluid, a linear encased segment acting as the microfluidic channel where sensors will be interfaced and an open large surface area segment providing the pumping energy via evaporation. Strip designs were created in CorelDraw and a $CO_2$ laser cutter (Universal Laser Systems VLS 3.5) was used to cut the paper strips.

Visual Dye Monitoring. Paper strips were placed on an acrylic sheet prior to testing with 1 cm of the linear segment hanging below. A 1 cm wide PDMS strip is placed over the top of the paper channel and pressed against the acrylic to hold the paper to the acrylic and limit evaporation in this region. A black piece of cardstock is then attached to the back side of the acrylic to act as a dark backdrop during obtain flow data. Matlab is used to obtain quantitative date from the series of images. This method is defined more in the Supplemental Document.

Electrical Sensing. Gold interdigitated electrodes were interfaced with the channel portion of the paper microfluidic device in our setup. The fingers on the electrode have widths of 50 μm and are spaced 25 μm apart. There are 29 total fingers, each with a length of 3 mm. The two leads on the electrodes were connected to a Gamry Reference 600 potentiostat on which single frequency potentiostatic electrochemical impedance measurements were performed at 1 MHz with 10 mV. Impedance was measured every 15 seconds.

Velocity Model and Limits.

The time delay between the moment a target analyte contacts the paper to the time it reaches a sensor along the path is determined by the geometrical design of the paper channel, including the area of the evaporation pad areas and the width and length of the paper "channel" connecting the collector and evaporation pads. The dye velocity through the devices was measured for paper devices of varying evaporation pad areas and channel widths. The data were interpreted based on a generalized fluid transport model that accounts for three factors: 1) evaporation rate based on pad size, 2) velocity of dye through the paper channel based on channel geometry (cross-sectional area) and 3) chromatographic effects between the dye and paper substrate. It also allowed us to identify the limitations to total fluid flowrate that arise from the hydrodynamic resistances encountered throughout the paper channel.

In order to evaluate the evaporation rate, we assume there is a constant evaporation flux (H) over the entire area (A) of the evaporation pad, as capillary action will keep the paper wetted. This assumption allows for the calculation of the mass flow rate of water (ṁ) going through the device is ṁ=HA. The flow rate of water through the paper channel in the microfluidic device can be obtained from a mass balance using the fluid velocity (v), channel width (w) and moisture content of the wet paper (M(mg/cm²)). This results in a mass flow of ṁ=vwM.

Chromatographic effects arising from the dye adsorption-desorption equilibria result in the dye lagging behind the fluid flow due to adsorption-desorption equilibria between the dye molecules in the fluid and the paper substrate. This lag can be taken into account by using a retardation factor ($R_f$), which correlates the dye velocity we observe to the actual velocity of fluid traveling through the paper micro-fluidic channel.

At steady state of complete device saturation with water, the mass of the evaporated water per unit time equals the mass flow rate through the channel. Incorporating the retardation factor and rearranging the equation allows for formulation of an equation for dye velocity. This model, plotted in FIG. 13A, fits the data well without any fitting parameters (as the value of $R_f$ used was measured independently).

$$v_{dye} = \frac{R_f HA}{wM} \tag{1}$$

Another flow regime is established when the water does not completely saturate the evaporation pad. Increasing the area of the pad increases the flow rate up to the point where the flow resistance of the channel limits the maximum flow rate. The flow rate in this regime is established by how rapidly the capillary wicking of fluid traveling through the device can replenish the evaporated fluid. The fluid transport through the paper channel encounters hydrodynamic resistance, which induces an associated pressure drop. Balancing this hydrodynamic pressure drop with the capillary pressure defines the maximum flow rate achievable through the channel. The pressure drop ($\Delta P$) over the channel length (L) can be correlated to the maximum flow of water ($Q_{max}$) through the paper device, viscosity ($\mu$), permeability ($\kappa$) and cross-sectional area (A) using Darcy's Law[39]:

$$\frac{\Delta P}{L} = -\frac{\mu}{\kappa A} Q_{max} \tag{2}$$

We assume that the pressure drop of the fluid in the evaporating pad is negligible due to its much larger cross-sectional area. The maximum flow rate is then limited by the maximum capillary wicking rate and equal to the flowrate expected from evaporation:

$$Q_{max} = \frac{\Delta P w h \kappa}{\mu L} = \frac{HA_{max}}{\rho} \tag{3}$$

A re-arrangement of this equation makes possible to evaluate the maximum wetted area ($A_{max}$) for a given channel width while the device is operating at its steady state:

$$A_{max} = \left(\frac{\Delta P h \kappa \rho}{\mu L H}\right) w \tag{4}$$

We measured the maximum area of water coverage with varying channel widths and large evaporating pads to verify $A_{max}$. The results are plotted in FIG. 13B. The maximum wetted area follows a linear relationship with channel width as predicted by the model. The deviation from the origin may be due to the neglected pressure drops in the evaporating pad or evaporation from the channel. This graph defines the parameter region in which the device operates at maximal efficiency (all of the evaporation pad is wetted, shaded area in FIG. 13B). Operation with evaporation pads with areas above this line result in a pad that is not fully saturated, as capillary wicking is not able to replenish water rapidly enough to fully saturate the pad area. Smaller evaporation areas can be used as evaporation becomes the limiting factor and capillary action is able to fully replenish evaporated water. These results reveal the flow-based limitations with evaporation-based pumping through a porous paper device.

Long Term Viability.

The limits of uninterrupted pumping were examined to determine the maximum operating lifetime. As mentioned, the key application of such devices that we foresee is in biological analysis of sweat as pumping and disposal component of wearable devices and patches. This means that they will have to operate for long time with biological solutions that contain dissolved salts and other species. These solutes will accumulate on the evaporation pad over time and will precipitate when their concentration exceeds the solubility limit. The resulting salt deposits will hinder the evaporation of fluid from the pad based on the increased osmotic pressure from higher salt concentration as well as physical obstruction from the precipitated salt crystals on the paper.

We evaluated the long-term operation of the paper strip devices with phosphate buffer solution (PBS) to observe the effects of salt accumulation on flow rate. PBS was used to simulate biological and medically relevant body fluids, such as sweat. The evaporative pumping of PBS results in the visible formation of a precipitated layer of salts at the outer edge of the evaporation pad. Surprisingly, the growth of this layer was gradual and slow. A solid salt layer is observed at the evaporation pad periphery by the second day of testing (FIG. 14A). The solid salt crust grew inwards from the evaporation pad periphery towards the center each day as more salt precipitated (FIG. 14B). However, in spite of the deposition of salt crust, the pumping process continues to operate for days on end.

In order to evaluate the long-term device performance, dye velocity was measured once a day over a 10 day span for multiple days (FIG. 14C). The area of the evaporation pad not covered in salt crystals was also measured daily (FIG. 14D). Both the dye velocity and uncovered area decrease over time as salt accumulates. Integration of the velocity over time shows a total fluid uptake of roughly 13 mL of solution. By comparison, a saturated paper strip of this size would contain 0.025 mL, approximately 1/500th of the amount of fluid pumped through evaporation. As a comparison, a 1 cm² interface on the forearm would produce an average sweat rate of roughly 0.75 μL/min[40]. At this sweat rate, it would take 289 hours (12+ days) before 13 mL is pumped and enough salt has precipitated to hinder the evaporative flow. This shows the viability of using this pumping mechanism as a long-term mechanism to be used in sweat sensing devices.

Dye velocity is proportional to the evaporating area, as shown in equation (1). That area available to evaporate water for pumping decreases over time as a direct result of salt accumulation. Thus, the rate of salt accumulation relates directly to flow rate. These correlations relate fluid velocity and area with $v=\alpha_1 A$ and $dA/dt=-\alpha_2 v$, where $\alpha_t$ corresponds to a constant. The solution for the rate of velocity and area decrease of this system of first order differential equations is exponential decay expressions, $$v = v_0 e^{-\frac{t}{\tau}} \tag{5}$$

$$A = A_0 e^{-\frac{t}{\tau}} \tag{6}$$

These dependencies match the data with good agreement. Both velocity and area on their own demonstrate exponential decay over a period of 10 days (FIGS. 14C-14D). The velocity and area remain linearly correlated to each other (FIG. 14E). This behavior of decreased evaporation rate due to an increase in concentrated and precipitated salt is broadly analogous to that of the evaporation of saline water from soil[41].

One issue that may be encountered in the long term operation of the device is the penetration of the exposed evaporation pad with external water or other contaminants. Such an undesired penetration can lead to device contamination and compromising of the precision. In order to avoid such contamination, the surface of the evaporation pad can be covered by a protective water-repellent porous layer. Such a layer, typically made of high surface area porous hydrophobic material will not hinder the continuous device operation, as the water from the collected sample can still evaporate through the pores, keeping the microfluidic pump operating. However, it will protect the external water splashes or contaminants from reaching the evaporation pad below them and hindering the device operation. The making of superhydrophobic porous materials could be achieved by a number of methods described earlier.

Sensing Demonstration.

These continual pumping paper microfluidic devices were tested to determine their operation in conjunction with several sensing mechanisms. Solutions with varying dye concentration (0-0.2%) were pumped through the paper channel, while measuring the resulting color over time. These tests were performed using multiple step changes as shown in FIG. 15A.

The response of the measured intensity to the change in sampled dye depends on the pumping rate and channel width. The steady state intensity was used to create a correlation curve with the dye concentration (FIG. 15B). There is a linear relationship between color intensity and dye concentration. This correlation was expected, as concentration of the dye is the only parameter altered and is directly correlated to color intensity. This result demonstrates the ability of this pumping device to be used for colorimetric sensing applications.

Many microfluidic sensing applications often involve electrochemical measurements through electrode arrays interfacing the sample in the channel (in this case a paper one). Interdigitated gold electrodes were pressed against the paper channel with the leads connected to a potentiostat (Gamry Reference 600) for high frequency (1 MHz) impedance testing. Solutions of varying NaCl concentration were pumped over time while recording the impedance response. The impedance signal changed rapidly in response to changes in the salt concentration in the collection pad (FIG. 15C). A correlation curve for impedance vs. salt concentration shows an inverse relationship between impedance and salt concentration ranging from low salinities, from 0.002 M, up to 0.25 M. Impedance leveled off at higher salt concentrations above this salinity, likely due to large surface impedances of the counterionic layers near the electrodes that dominate the measured impedance.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A microfluidic device comprising:
a porous hydrophilic substrate having both an upper surface and a lower surface, wherein the lower surface is configured to be in contact with skin, wherein the porous hydrophilic substrate comprising a collection pad, an evaporative pump, and a closed channel connecting the collection pad and the evaporative pump, wherein the collection pad is located only on the lower surface of the porous hydrophilic substrate, wherein the evaporative pump comprises an evaporation pad, wherein the evaporation pad comprises a first cellulosic substrate, wherein the evaporation pad is located only on the upper surface of the porous hydrophilic substrate, wherein the evaporation pad and the collection pad are located on opposite surfaces of the porous hydrophilic substrate, wherein a side of the closed channel is made of a second cellulosic substrate; and
a hydrogel in contact with the upper surface of the porous hydrophilic substrate at the collection pad, wherein the porous hydrophilic substrate is between the hydrogel and the skin, wherein the hydrogel comprises a plurality of extractants.

2. The microfluidic device according to claim 1, wherein the first cellulosic substrate is selected from the group consisting of paper, cellulose derivatives, woven cellulosic materials, and non-woven cellulosic materials, wherein the second cellulosic substrate is selected from the group consisting of paper, cellulose derivatives, woven cellulosic materials, and non-woven cellulosic materials.

3. The microfluidic device according to claim 2, wherein the first cellulosic substrate is paper that is selected from the group consisting of filter paper, chromatography paper, card stock, vellum paper, printing paper, bond paper, blotting paper, drawing paper, tissue paper, paper towel, and nanocelluosic paper, wherein the second cellulosic substrate is paper that is selected from the group consisting of filter paper, chromatography paper, card stock, vellum paper, printing paper, bond paper, blotting paper, drawing paper, tissue paper, paper towel, and nanocelluosic paper.

4. The microfluidic device according to claim 2, wherein the first cellulosic substrate is paper having a grammage of about 0.5 $g/m^2$ or more, wherein the second cellulosic substrate is paper having a grammage of about 0.5 $g/m^2$ or more.

5. The microfluidic device according to claim 1, wherein the porous hydrophilic substrate has a thickness of about 0.05 mm to 0.5 mm.

6. The microfluidic device according to claim 1, wherein the collection pad has a surface area of about 1 mm$^2$ to 100 mm$^2$.

7. The microfluidic device according to claim 1, wherein the closed channel has a width of about 100 µm to 1000 µm.

8. The microfluidic device according to claim 1, wherein the closed channel has a height of about 5 µm to 500 µm.

9. The microfluidic device according to claim 1, wherein the closed channel has a length of about 5 mm to 30 mm.

10. The microfluidic device according to claim 1, wherein the evaporative pump comprises the evaporation pad has surface area of about 0.1 cm$^2$ to 10 cm$^2$.

11. The microfluidic device according to claim 1, wherein the evaporation pad has a surface area of about 0.1 cm$^2$ to about A$_{max}$, wherein A$_{max}$ is calculated according to the following formula $$A_{max} = \left( \frac{\Delta P h \kappa \rho}{\mu L H} \right) w$$

where ρ is a density of a fluid, L is a length of the closed channel, h is height of the closed channel, w is a width of the closed channel, µ is a viscosity of the fluid flowing through the closed channel, κ is a permeability of the fluid flowing through the channel, ΔP is a pressure drop over the length of the closed channel, and H is an evaporation flux of the evaporation pad.

12. The microfluidic device according to claim 11, wherein the fluid is selected from the group consisting of sweat, interstitial fluid, extracellular fluid, blood, urine, saliva, tissue exudate, tissue transudate, and a combination thereof.

13. The microfluidic device according to claim 12, wherein the fluid comprises a hydrophilic fluid.

14. The microfluidic device according to claim 1, wherein the evaporation pad is a semicircular or radial segment evaporation pad composed of paper, extending radially from an end of the closed channel.

15. The microfluidic device according to claim 1, wherein the hydrogel comprises a crosslinked network comprising one or more hydrophilic polymers or biopolymers.

16. A method of detecting an analyte in a fluid using a microfluidic device according to claim 1, the method comprising placing the lower surface of the microfluidic device on the skin so that the collection pad is in contact with the skin, and measuring the analyte in the fluid by detecting the amount of analyte collected either in the closed channel or in the evaporative pump.

17. A microfluidic device comprising:

a porous hydrophilic substrate, wherein the porous hydrophilic substrate is a single layer having both an upper surface and a lower surface, wherein the lower surface is configured to be in contact with skin, wherein the porous hydrophilic substrate comprising a collection pad, an evaporative pump, and a closed channel connecting the collection pad and the evaporative pump, wherein the evaporative pump comprises an evaporation pad, wherein the evaporation pad comprises a first cellulosic substrate, wherein a side of the closed channel is made of a second cellulosic substrate; and a hydrogel in contact with the upper surface of the porous hydrophilic substrate at the collection pad, wherein the porous hydrophilic substrate is between the hydrogel and the skin, wherein the hydrogel comprises a plurality of extractants;

wherein the collection pad is located only on the lower surface of the porous hydrophilic substrate, wherein the evaporation pad is located only on the upper surface of the porous hydrophilic substrate, and wherein the evaporation pad and the collection pad are located on opposite surfaces of the porous hydrophilic substrate.

* * * * *